(12) United States Patent
Rosen et al.

(10) Patent No.: US 10,327,888 B2
(45) Date of Patent: Jun. 25, 2019

(54) ENHANCED TORIC LENS THAT IMPROVES OVERALL VISION WHERE THERE IS A LOCAL LOSS OF RETINAL FUNCTION

(71) Applicant: AMO GRONINGEN B.V., Groningen (NL)

(72) Inventors: Robert Rosen, Groningen (NL); Hendrik A. Weeber, Groningen (NL); Carmen Canovas Vidal, Groningen (NL); Marrie Van Der Mooren, Engelbert (NL); Dora Sellitri, Matera (IT)

(73) Assignee: AMO GRONINGEN B.V., Groningen (NL)

( * ) Notice: Subject to any disclaimer, the term of this patent is extended or adjusted under 35 U.S.C. 154(b) by 0 days.

(21) Appl. No.: 15/472,084

(22) Filed: Mar. 28, 2017

(65) Prior Publication Data

US 2017/0196683 A1    Jul. 13, 2017

Related U.S. Application Data

(62) Division of application No. 14/644,110, filed on Mar. 10, 2015, now Pat. No. 9,636,215.
(Continued)

(51) Int. Cl.
*A61F 2/16* (2006.01)
*A61B 3/14* (2006.01)
(Continued)

(52) U.S. Cl.
CPC .......... *A61F 2/1656* (2013.01); *A61B 3/0025* (2013.01); *A61B 3/028* (2013.01);
(Continued)

(58) Field of Classification Search
CPC ...... A61F 2/164; A61F 2/1605; A61F 2/1659; A61F 2/1618; A61F 2/1637;
(Continued)

(56) References Cited

U.S. PATENT DOCUMENTS

| | | |
|---|---|---|
| 3,367,734 A | 2/1968 | Bystricky et al. |
| 4,581,031 A | 4/1986 | Koziol et al. |

(Continued)

FOREIGN PATENT DOCUMENTS

| | | |
|---|---|---|
| EP | 0343067 A1 | 11/1989 |
| EP | 0457553 A2 | 11/1991 |

(Continued)

OTHER PUBLICATIONS

International Search Report and Written Opinion for Application No. PCT/IB2017/000553, dated Aug. 28, 2017, 19 pages.
(Continued)

*Primary Examiner* — Paul B Prebilic
(74) *Attorney, Agent, or Firm* — Johnson & Johnson Surgical Vision, Inc.

(57) ABSTRACT

Systems and methods are provided for improving overall vision in patients suffering from a loss of vision in a portion of the retina (e.g., loss of central vision) by providing an enhanced toric lens which redirects and/or focuses light incident on the eye at oblique angles onto a peripheral retinal location. The intraocular lens can include a redirection element (e.g., a prism, a diffractive element, or an optical component with a decentered GRIN profile) configured to direct incident light along a deflected optical axis and to focus an image at a location on the peripheral retina. Optical properties of the intraocular lens can be configured to improve or reduce peripheral errors at the location on the peripheral retina. One or more surfaces of the intraocular
(Continued)

lens can be a toric surface, a higher order aspheric surface, an aspheric Zernike surface or a Biconic Zernike.

15 Claims, 13 Drawing Sheets

Related U.S. Application Data

(60) Provisional application No. 61/987,647, filed on May 2, 2014, provisional application No. 61/950,757, filed on Mar. 10, 2014.

(51) Int. Cl.
| | | |
|---|---|---|
| *A61B 3/028* | (2006.01) | |
| *A61B 3/00* | (2006.01) | |
| *A61B 3/10* | (2006.01) | |
| *A61B 3/103* | (2006.01) | |
| *A61B 3/107* | (2006.01) | |

(52) U.S. Cl.
CPC ............ *A61B 3/103* (2013.01); *A61B 3/1005* (2013.01); *A61B 3/107* (2013.01); *A61B 3/14* (2013.01); *A61F 2/1602* (2013.01); *A61F 2/164* (2015.04); *A61F 2/1613* (2013.01); *A61F 2/1618* (2013.01); *A61F 2/1637* (2013.01); *A61F 2/1645* (2015.04); *A61F 2/1648* (2013.01); *A61F 2/1654* (2013.01); *A61F 2/1605* (2015.04); *A61F 2/1659* (2013.01); *A61F 2002/1681* (2013.01); *A61F 2240/002* (2013.01)

(58) Field of Classification Search
CPC .... A61F 2/1645; A61F 2/1648; A61F 2/1602; A61F 2/1656; A61F 2002/1681; A61F 2240/002; A61F 2250/0091
See application file for complete search history.

(56) References Cited

U.S. PATENT DOCUMENTS

| | | | |
|---|---|---|---|
| 4,624,538 | A | 11/1986 | MacFarlane |
| 4,637,697 | A | 1/1987 | Freeman |
| 4,642,112 | A | 2/1987 | Freeman |
| 4,648,878 | A | 3/1987 | Kelman |
| 4,655,565 | A | 4/1987 | Freeman |
| 4,666,446 | A | 5/1987 | Koziol et al. |
| 4,778,462 | A | 10/1988 | Grendahl |
| 4,795,462 | A | 1/1989 | Grendahl |
| 4,798,608 | A | 1/1989 | Grendahl |
| 4,798,609 | A | 1/1989 | Grendahl |
| 4,828,558 | A | 5/1989 | Kelman |
| 4,932,970 | A | 6/1990 | Portney |
| 4,995,714 | A | 2/1991 | Cohen |
| 4,995,715 | A | 2/1991 | Cohen |
| 5,016,977 | A | 5/1991 | Baude et al. |
| 5,056,908 | A | 10/1991 | Cohen |
| 5,066,301 | A | 11/1991 | Wiley |
| 5,089,023 | A | 2/1992 | Swanson |
| 5,096,285 | A | 3/1992 | Silberman |
| 5,114,220 | A | 5/1992 | Baude et al. |
| 5,117,306 | A | 5/1992 | Cohen |
| 5,120,120 | A | 6/1992 | Cohen |
| 5,121,979 | A | 6/1992 | Cohen |
| 5,121,980 | A | 6/1992 | Cohen |
| 5,144,483 | A | 9/1992 | Cohen |
| 5,225,858 | A | 7/1993 | Portney |
| 5,229,797 | A | 7/1993 | Futhey et al. |
| 5,354,334 | A | 10/1994 | Fedorov et al. |
| 5,549,669 | A | 8/1996 | Jansen |
| 5,652,638 | A | 7/1997 | Roffman et al. |
| 5,683,457 | A | 11/1997 | Gupta et al. |
| 5,699,142 | A | 12/1997 | Lee et al. |
| 5,728,156 | A | 3/1998 | Gupta et al. |
| 5,748,282 | A | 5/1998 | Freeman |
| 5,760,871 | A | 6/1998 | Kosoburd et al. |
| 5,777,719 | A | 7/1998 | Williams et al. |
| 5,796,462 | A | 8/1998 | Roffman et al. |
| 5,968,094 | A | 10/1999 | Werblin et al. |
| 6,126,283 | A | 10/2000 | Wen et al. |
| 6,126,286 | A | 10/2000 | Portney |
| 6,142,625 | A | 11/2000 | Sawano et al. |
| 6,183,084 | B1 | 2/2001 | Chipman et al. |
| 6,197,057 | B1 | 3/2001 | Peyman et al. |
| 6,210,005 | B1 | 4/2001 | Portney |
| 6,338,559 | B1 | 1/2002 | Williams et al. |
| 6,457,826 | B1 | 10/2002 | Lett |
| 6,464,355 | B1 | 10/2002 | Gil |
| 6,474,814 | B1 | 11/2002 | Griffin |
| 6,488,708 | B2 | 12/2002 | Sarfarazi |
| 6,491,721 | B2 | 12/2002 | Freeman et al. |
| 6,527,389 | B2 | 3/2003 | Portney |
| 6,533,416 | B1 | 3/2003 | Fermigier et al. |
| 6,533,814 | B1 | 3/2003 | Jansen |
| 6,536,899 | B1 | 3/2003 | Fiala |
| 6,537,317 | B1 | 3/2003 | Steinert et al. |
| 6,547,822 | B1 | 4/2003 | Lang |
| 6,554,859 | B1 | 4/2003 | Lang et al. |
| 6,557,992 | B1 | 5/2003 | Dwyer et al. |
| 6,609,793 | B2 | 8/2003 | Norrby et al. |
| 6,705,729 | B2 | 3/2004 | Piers et al. |
| 6,808,262 | B2 | 10/2004 | Chapoy et al. |
| 6,830,332 | B2 | 12/2004 | Piers et al. |
| 6,846,326 | B2 | 1/2005 | Zadno-Azizi et al. |
| 6,851,803 | B2 | 2/2005 | Wooley et al. |
| 6,913,620 | B2 | 7/2005 | Lipshitz |
| 6,923,539 | B2 | 8/2005 | Simpson et al. |
| 6,923,540 | B2 | 8/2005 | Ye et al. |
| 6,986,578 | B2 | 1/2006 | Jones |
| 7,025,456 | B2 | 4/2006 | Morris et al. |
| 7,025,460 | B2 | 4/2006 | Smitth, III |
| 7,036,931 | B2 | 5/2006 | Lindacher |
| 7,048,760 | B2 | 5/2006 | Cumming |
| 7,061,693 | B2 | 6/2006 | Zalevsky |
| 7,073,906 | B1 | 7/2006 | Portney |
| 7,137,702 | B2 | 11/2006 | Piers et al. |
| 7,156,516 | B2 | 1/2007 | Morris et al. |
| 7,186,266 | B2 | 3/2007 | Peyman |
| 7,188,949 | B2 | 3/2007 | Bandhauer et al. |
| 7,238,201 | B2 | 7/2007 | Portney et al. |
| 7,287,852 | B2 | 10/2007 | Fiala |
| 7,293,873 | B2 | 11/2007 | Dai et al. |
| 7,365,917 | B2 | 4/2008 | Zalevsky |
| 7,377,640 | B2 | 5/2008 | Piers et al. |
| 7,410,500 | B2 | 8/2008 | Claoue |
| 7,441,894 | B2 | 10/2008 | Zhang et al. |
| 7,475,986 | B2 | 1/2009 | Dai et al. |
| 7,503,655 | B2 | 3/2009 | Smith, III |
| 7,615,073 | B2 | 11/2009 | Deacon et al. |
| 7,665,842 | B2 | 2/2010 | Ho et al. |
| 7,766,482 | B2 | 8/2010 | Smith, III et al. |
| 7,871,162 | B2 | 1/2011 | Weeber |
| 7,997,727 | B2 | 8/2011 | Ho et al. |
| 8,057,034 | B2 | 11/2011 | Ho et al. |
| 8,062,361 | B2 | 11/2011 | Nguyen et al. |
| 8,201,943 | B2 | 6/2012 | Hammer et al. |
| 8,206,442 | B2 | 6/2012 | Sel et al. |
| 8,262,728 | B2 | 9/2012 | Zhang et al. |
| 8,382,832 | B2 | 2/2013 | Deacon et al. |
| 8,430,508 | B2 | 4/2013 | Weeber |
| 8,540,365 | B2 | 9/2013 | Varnas |
| 8,862,447 | B2 | 10/2014 | Weeber |
| 9,345,570 | B2 | 5/2016 | Sieber et al. |
| 9,579,192 | B2 * | 2/2017 | Rosen .............. A61B 3/14 |
| 9,867,693 | B2 * | 1/2018 | Rosen .............. A61B 3/14 |
| 10,143,548 | B2 * | 12/2018 | Rosen .............. A61B 3/14 |
| 2002/0044255 | A1 | 4/2002 | Ye |
| 2002/0101564 | A1 | 8/2002 | Herrick |
| 2002/0118337 | A1 | 8/2002 | Perrott et al. |
| 2002/0176049 | A1 | 11/2002 | Sakai et al. |
| 2003/0076478 | A1 | 4/2003 | Cox |
| 2003/0171808 | A1 | 9/2003 | Phillips |

(56) References Cited

U.S. PATENT DOCUMENTS

| | | |
|---|---|---|
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0156013 A1* | 8/2004 | Lindacher ............ A61F 2/1613 351/159.41 |
| 2004/0156014 A1 | 8/2004 | Piers et al. |
| 2005/0096226 A1 | 5/2005 | Stock et al. |
| 2005/0128432 A1 | 6/2005 | Altmann |
| 2005/0203619 A1 | 9/2005 | Altmann |
| 2006/0009816 A1 | 1/2006 | Fang et al. |
| 2006/0030938 A1 | 2/2006 | Altmann |
| 2006/0058874 A1 | 3/2006 | Peli |
| 2006/0066808 A1 | 3/2006 | Blum et al. |
| 2006/0098162 A1 | 5/2006 | Bandhauer et al. |
| 2006/0109421 A1 | 5/2006 | Ye et al. |
| 2006/0116763 A1* | 6/2006 | Simpson ............... A61F 2/1613 623/6.23 |
| 2006/0116764 A1 | 6/2006 | Simpson |
| 2006/0116765 A1 | 6/2006 | Blake et al. |
| 2006/0158611 A1 | 7/2006 | Piers et al. |
| 2006/0227286 A1 | 10/2006 | Hong et al. |
| 2006/0238702 A1 | 10/2006 | Glick et al. |
| 2006/0244904 A1 | 11/2006 | Hong et al. |
| 2006/0247766 A1 | 11/2006 | Marin |
| 2007/0052920 A1 | 3/2007 | Stewart et al. |
| 2007/0093891 A1 | 4/2007 | Tabernero et al. |
| 2007/0129803 A1 | 6/2007 | Cumming et al. |
| 2007/0171362 A1 | 7/2007 | Simpson et al. |
| 2007/0182924 A1 | 8/2007 | Hong et al. |
| 2007/0268453 A1 | 11/2007 | Hong et al. |
| 2008/0030677 A1 | 2/2008 | Simpson |
| 2008/0161913 A1 | 7/2008 | Brady et al. |
| 2008/0161914 A1 | 7/2008 | Brady et al. |
| 2008/0269883 A1 | 10/2008 | Das et al. |
| 2008/0269885 A1 | 10/2008 | Simpson et al. |
| 2008/0269886 A1 | 10/2008 | Simpson et al. |
| 2008/0269890 A1 | 10/2008 | Simpson et al. |
| 2008/0312738 A1 | 12/2008 | Wanders |
| 2009/0018652 A1 | 1/2009 | Hermans et al. |
| 2009/0062911 A1 | 3/2009 | Bogaert |
| 2009/0164008 A1 | 6/2009 | Hong et al. |
| 2009/0187242 A1 | 7/2009 | Weeber et al. |
| 2009/0198326 A1 | 8/2009 | Zhou et al. |
| 2009/0204211 A1 | 8/2009 | Angelopoulos et al. |
| 2009/0210054 A1 | 8/2009 | Weeber et al. |
| 2009/0234448 A1 | 9/2009 | Weeber et al. |
| 2009/0268155 A1 | 10/2009 | Weeber |
| 2009/0292354 A1 | 11/2009 | Gontijo et al. |
| 2009/0295295 A1 | 12/2009 | Shannon et al. |
| 2009/0323020 A1 | 12/2009 | Zhao et al. |
| 2010/0016961 A1 | 1/2010 | Hong et al. |
| 2010/0100177 A1 | 4/2010 | Zhao |
| 2010/0100178 A1 | 4/2010 | Weeber et al. |
| 2010/0157240 A1 | 6/2010 | Schmid et al. |
| 2010/0161048 A1 | 6/2010 | Schaper, Jr. |
| 2010/0188636 A1 | 7/2010 | Pinto et al. |
| 2011/0130833 A1 | 6/2011 | Scott et al. |
| 2011/0153014 A1 | 6/2011 | Zhang et al. |
| 2011/0279912 A1 | 11/2011 | Fiala |
| 2012/0277857 A1 | 11/2012 | Purchase et al. |
| 2013/0013060 A1 | 1/2013 | Zadno-Azizi et al. |
| 2013/0211515 A1 | 8/2013 | Blum et al. |
| 2013/0226294 A1 | 8/2013 | Van Der Mooren et al. |
| 2014/0022649 A1 | 1/2014 | Eckhardt |
| 2014/0168602 A1 | 6/2014 | Weeber et al. |
| 2014/0253877 A1 | 9/2014 | Li et al. |
| 2015/0005877 A1 | 1/2015 | Wanders |
| 2015/0250583 A1 | 9/2015 | Rosen et al. |
| 2015/0250585 A1 | 9/2015 | Rosen et al. |
| 2015/0265399 A1 | 9/2015 | Rosen et al. |
| 2015/0297342 A1 | 10/2015 | Rosen et al. |
| 2015/0320547 A1 | 11/2015 | Rosen et al. |
| 2016/0067037 A1 | 3/2016 | Rosen et al. |
| 2016/0161364 A1 | 6/2016 | Alarcon et al. |
| 2016/0193040 A1* | 7/2016 | Qureshi ............... A61F 2/1613 623/6.23 |

FOREIGN PATENT DOCUMENTS

| | | |
|---|---|---|
| EP | 458508 A2 | 11/1991 |
| EP | 681198 A1 | 11/1995 |
| EP | 0926531 A1 | 6/1999 |
| EP | 949529 A2 | 10/1999 |
| EP | 1818023 A1 | 8/2007 |
| EP | 1284687 B1 | 12/2007 |
| EP | 1310267 B1 | 1/2008 |
| EP | 1424049 B1 | 6/2009 |
| WO | 9222264 A1 | 12/1992 |
| WO | 9303409 A1 | 2/1993 |
| WO | 0019906 A1 | 4/2000 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 03000154 A2 | 1/2003 |
| WO | 03009053 A1 | 1/2003 |
| WO | 03022137 A2 | 3/2003 |
| WO | 2004034129 A1 | 4/2004 |
| WO | 2004049979 A1 | 6/2004 |
| WO | 2004068214 A1 | 8/2004 |
| WO | 04090611 A2 | 10/2004 |
| WO | 04096014 A2 | 11/2004 |
| WO | 05019906 A1 | 3/2005 |
| WO | 06025726 A1 | 3/2006 |
| WO | 06047698 A1 | 5/2006 |
| WO | 06060477 A2 | 6/2006 |
| WO | 06060480 A2 | 6/2006 |
| WO | 2006067255 A1 | 6/2006 |
| WO | 2007092948 A1 | 8/2007 |
| WO | 2007133384 A2 | 11/2007 |
| WO | 2008045847 A2 | 4/2008 |
| WO | 2008065362 A1 | 6/2008 |
| WO | 2009076670 A1 | 6/2009 |
| WO | 2009142961 A1 | 11/2009 |
| WO | 2012074742 A1 | 6/2012 |
| WO | 2012083143 A1 | 6/2012 |
| WO | 2013028992 A1 | 2/2013 |
| WO | 2013059041 A1 | 4/2013 |
| WO | 2013105855 A1 | 7/2013 |
| WO | 2013185855 A1 | 12/2013 |
| WO | 2015136375 A2 | 9/2015 |
| WO | 2015136380 A2 | 9/2015 |

OTHER PUBLICATIONS

International Search Report and Written Opinion for Application No. PCT/IB2017/000318, dated Aug. 4, 2017, 14 pages.

Alfonso J.F., et al., "Prospective Study of the Acri.LISA Bifocal Intraocular Lens," Journal of Cataract Refractive Surgery, Nov. 2007, vol. 33 (11), pp. 1930-1935.

Atchison D.A., et al., "Shape of the Retinal Surface in Emmetropia and Myopia," Investigative Ophthalmology & Visual Science, Aug. 2005, vol. 46 (8), pp. 2698-2707.

Baskaran K., et al., "Benefit of Adaptive Optics Aberration Correction at Preferred Retinal Locus," Optometry and Vision Science, Sep. 2012, vol. 89 (9), pp. 1417-1423.

Buralli D.A., et al, "Optical Performance of Holographic Kinoforms," Applied Optics, Mar. 1989, vol. 28 (5), pp. 976-983.

Canovas C., et al., "Hybrid Adaptive-Optics Visual Simulator," Optical Letters, Jan. 15, 2010, vol. 35 (2), pp. 196-198.

Cohen A.L., "Practical Design of a Bifocal Hologram Contact Lens or Intraocular Lens," Applied Optics, Jul. 1, 1992, vol. 31 (19), pp. 3750-3754.

Diffractive Lenses for Extended Depth of Focus and Presbyopic Correction, Presentation from Wavefront Congress held on Feb. 15, 2008, Rochester, New York.

Doskolovich L.L., et al., "Special Diffractive Lenses," Lens and Optical Systems Design, Apr. 1992, vol. 1780, pp. 393-402.

(56) References Cited

OTHER PUBLICATIONS

Escudero-Sanz I., et al., "Off-Axis Aberrations of a Wide-Angle Schematic Eye Model," Journal of the Optical Society of America. A, Optics, Image Science, and Vision, Aug. 1999, vol. 16 (8), pp. 1881-1891.

Hoffmann, P.C., et al., "Analysis of Biometry and Prevalence Data for Corneal Astigmatism in 23 239 Eyes," Journal of Cataract and Refractive Surgery, Sep. 2010, vol. 36(9), pp. 1479-1485.

International Search Report and Written Opinion for Application No. PCT/IB2015/000989, dated Sep. 8, 2015, 13 pages.

International Search Report and Written Opinion for Application No. PCT/IB2015/001027, dated Sep. 8, 2015, 14 pages.

International Search Report and Written Opinion for Application No. PCT/IB2015/001244, dated Nov. 8, 2015, 14 pages.

International Search Report and Written Opinion for Application No. PCT/IB2015/001588, dated Oct. 15, 2015, 11 pages.

International Search Report and Written Opinion for Application No. PCT/IB2015/002000, dated Feb. 12, 2016, 12 pages.

International Search Report and Written Opinion for Application No. PCT/US2012/052311, dated Dec. 21, 2012, 14 pages.

International Search Report and Written Opinion for Application No. PCT/US2014/020343, dated May 15, 2014, 10 pages.

Jaeken B., et al., "Comparison of the Optical Image Quality in the Periphery of Phakic and Pseudophakic Eyes," Investigative Ophthalmology & Visual Science, May 1, 2013, vol. 54 (5), pp. 3594-3599.

Jafari-Nodoushan M., et al., "Control-Flow Checking Using Branch Instructions," IEEE/IFIP International Conference on Embedded and Ubiquitous Computing, Dec. 17-20, 2008, pp. 66-72.

Lewis P., et al., "Resolution of Static and Dynamic Stimuli in the Peripheral Visual Field," Vision Research, Aug. 15, 2011, vol. 51 (16), pp. 1829-1834.

Liou H.L., et al., "Anatomically Accurate, Finite Model Eye for Optical Modeling," Journal of Optical Society of America, Aug. 1997, vol. 14 (8), pp. 1684-1695.

Liou H.L., et al., "The Prediction of Spherical Aberration with Schematic Eyes," Ophthalmic and Physiological Optics, Jan. 1996, vol. 16 (4), pp. 348-354.

Lundstroma L., et al., "Symmetries in Peripheral Ocular Aberrations," Journal of Modern Optics, Mar. 16, 2011, vol. 58 (19-20), pp. 1690-1695.

Marsack J.D., et al., "Metrics of Optical Quality Derived from Wave Aberrations Predict Visual Performance," Journal of Vision, Apr. 2004, vol. 4 (4), pp. 322-328.

Monsoriu J.A., et al., "Devil's Lenses," Optics Express, Oct. 17, 2007, vol. 15 (21), pp. 13858-13864.

Norrby S., et al., "Model Eyes for Evaluation of Intraocular Lenses," Applied Optics, Sep. 7, 2007, vol. 46 (26), pp. 6595-6605.

Oh N., et al., "Control-Flow Checking by Software Signatures," IEEE Transactions on Reliability, Mar. 2, 2002, vol. 51 (2), pp. 111-122.

Piers P.A., et al., "Eye Models for the Prediction of Contrast Vision in Patients with New Intraocular Lens Designs," Optics Letters, Apr. 1, 2004, vol. 29 (7), pp. 733-735.

Piers P.A., et al., "Theoretical Comparison of Aberration-Correcting Customized and Aspheric Intraocular Lenses," Journal of Refractive Surgery, Apr. 2007, vol. 23 (4), pp. 374-384.

Rosen R., et al., "Adaptive Optics for Peripheral Vision," Journal of Modern Optics, Jul. 10, 2012, vol. 59 (12), pp. 1064-1070.

Rosen R., et al., "Evaluating the Peripheral Optical Effect of Multifocal Contact Lenses," Ophthalmic and Physiological Optics, Nov. 2012, vol. 32 (6), pp. 527-534.

Rosen R., et al., "Have We Misinterpreted the Study of Hoogerheide Et Al. (1971)?," Optometry and Vision Science, Aug. 2012, vol. 89 (8), pp. 1235-1237.

Rosen R., et al., "Sign-dependent Sensitivity to Peripheral Defocus for Myopes Due to Aberrations," Investigative Ophthalmology & Visual Science, Oct. 17, 2012, vol. 53 (11), pp. 7176-7182.

Rosen R., et al., "Influence of Optical Defocus on Peripheral Vision," Visual Psychophysics and Physiological Optics, Jan. 2011, vol. 52 (1), pp. 318-323.

Rosen R., "Peripheral Vision: Adaptive Optics and Psychophysics," Doctoral Thesis Department of Applied Physics Royal Institute of Technology Stockholm, Sweden Apr. 2013, 86 pages.

Siedlecki D., et al., "Radial Gradient index Intraocular Lens: a Theoretical Model," Journal of Modern Optics, Feb. 20-Mar. 10, 2008, vol. 55 (4-5), pp. 639-647.

Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.

Van Den Berg T.J., "Analysis of Intraocular Straylight, Especially in Relation to Age," Optometry and Vision Science, Feb. 1995, vol. 72 (2), pp. 52-59.

Van Meeteren A., "Calculations on the Optical Modulation Transfer Function of the Human Eye for White Light," Optica Acta, May 1974, vol. 21 (5), pp. 395-412.

Villegas E.A., et al., "Correlation between Optical and Psychophy, Sical Parameters as a Function of Defocus," Optometry and Vision Science, Jan. 1, 2002, vol. 79 (1), pp. 60-67.

* cited by examiner

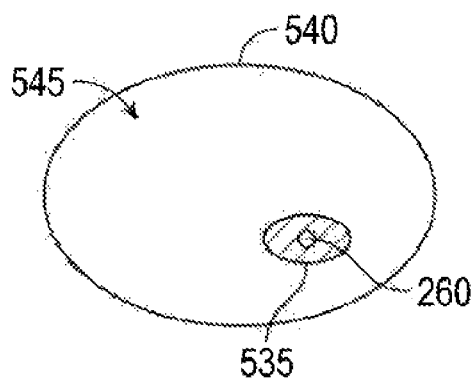
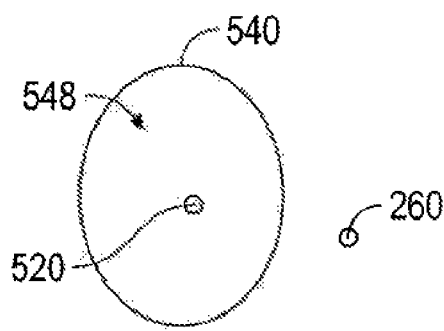
FIG. 5D-1                FIG. 5D-2
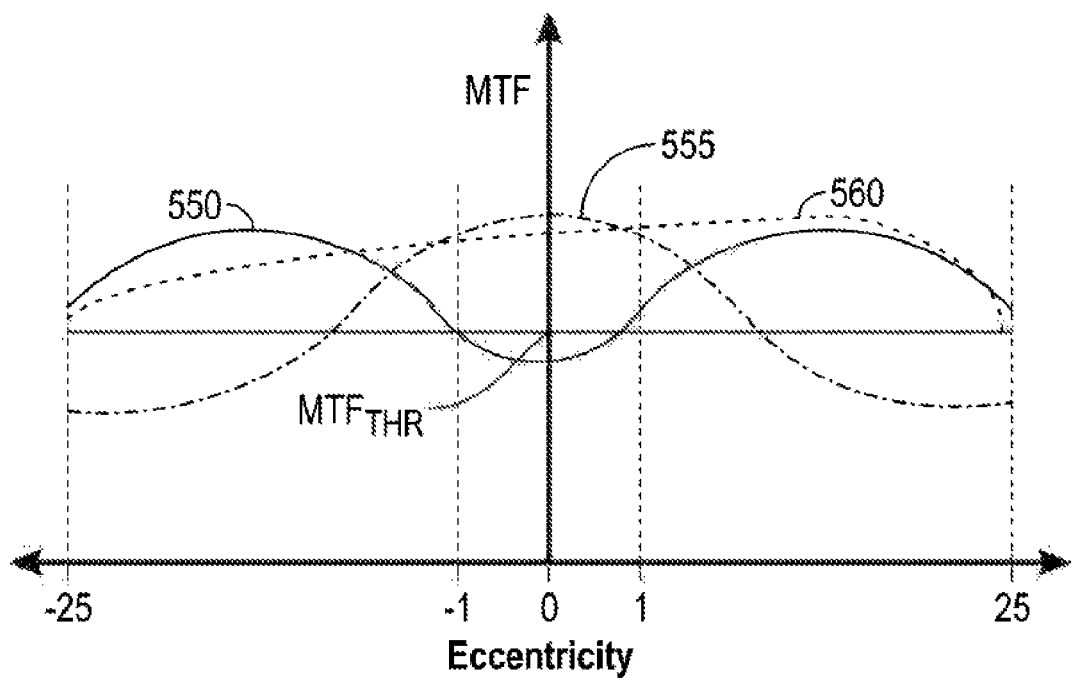
FIG. 5E

ENHANCED TORIC LENS THAT IMPROVES OVERALL VISION WHERE THERE IS A LOCAL LOSS OF RETINAL FUNCTION

CROSS-REFERENCE TO RELATED APPLICATIONS

This application is a divisional of and claims priority to U.S. patent application Ser. No. 14/644,110, filed Mar. 10, 2015, now U.S. Pat. No. 9,636,215, which claims benefit under 35 U.S.C. § 119(e) of U.S. Provisional Application No. 61/950,757, filed on Mar. 10, 2014, titled "INTRAOCULAR LENS THAT IMPROVES OVERALL VISION WHERE THERE IS A LOSS OF CENTRAL VISION." This application also claims benefit under 35 U.S.C. § 119(e) of U.S. Provisional Application No. 61/987,647, filed on May 2, 2014. The entire content of each of the above identified applications is incorporated by reference herein in its entirety for all it discloses and is made part of this specification.

This application is also related to U.S. application Ser. No. 14/644,082, filed concurrently herewith on Mar. 10, 2015, titled "INTRAOCULAR LENS THAT IMPROVES OVERALL VISION WHERE THERE IS A LOCAL LOSS OF RETINAL FUNCTION". This application is also related to U.S. application Ser. No. 14/644,101, filed concurrently herewith on Mar. 10, 2015, titled "DUAL-OPTIC INTRAOCULAR LENS THAT IMPROVES OVERALL VISION WHERE THERE IS A LOCAL LOSS OF RETINAL FUNCTION,". This application is also related to U.S. application Ser. No. 14/644,107, filed concurrently herewith on Mar. 10, 2015, titled "PIGGYBACK INTRAOCULAR LENS THAT IMPROVES OVERALL VISION WHERE THERE IS A LOCAL LOSS OF RETINAL FUNCTION,". The entire content of each of the above identified applications is incorporated by reference herein in its entirety for all it discloses and is made part of this specification.

BACKGROUND

Field

This disclosure generally relates to using an intraocular lens to improve overall vision where there is a local loss of retinal function (e.g., loss of central vision due to a central scotoma), and more particularly to using an intraocular lens to focus light incident at oblique angles on the patient's eye onto a location of the peripheral retina.

Description of Related Art

Surgery on the human eye has become commonplace in recent years. Many patients pursue eye surgery to treat an adverse eye condition, such as cataract, myopia and presbyopia. One eye condition that can be treated surgically is age-related macular degeneration (AMD). Other retinal disorders affect younger patients. Examples of such diseases include Stargardt disease and Best disease. Also, a reverse form of retinitis pigmentosa produces an initial degradation of central vision. A patient with AMD suffers from a loss of vision in the central visual field due to damage to the retina. Patients with AMD rely on their peripheral vision for accomplishing daily activities. A major cause of AMD is retinal detachment which can occur due to accumulation of cellular debris between the retina and the vascular layer of the eye (also referred to as "choroid") or due to growth of blood vessels from the choroid behind the retina. In one type of AMD, damage to the macula can be arrested with the use of medicine and/or laser treatment if detected early. If the degradation of the retina can be halted a sustained vision benefit can be obtained with an IOL. For patients with continued degradation in the retina a vision benefit is provided at least for a time.

SUMMARY

The systems, methods and devices of the disclosure each have several innovative aspects, no single one of which is solely responsible for the desirable attributes disclosed herein.

Ophthalmic devices that magnify images on the retina can be used to improve vision in patients suffering from AMD. Such ophthalmic devices can include a high optical power loupe or a telescope. Intraocular lenses (IOLs) that magnify images on the retina can also be implanted to improve vision in patients suffering from AMD. Such IOLs are based on a telescopic effect and can magnify images between about 1.3 times and about 2.5 times, which will improve resolution at the cost of a reduced visual field. However, such IOLs may not provide increased contrast sensitivity.

Various embodiments disclosed herein include ophthalmic devices (such as, for example, IOLs, contact lenses, etc.) that take into consideration the retinal structure and image processing capabilities of the peripheral retina to improve vision in patients suffering from AMD. The ophthalmic devices described herein can be lightweight and compact. Various embodiments of the ophthalmic devices described herein can focus incident light in a region around the fovea, such that a patient can move the eye and choose a direction that provides the best vision. For patients with a developed preferred area of the peripheral retina, the embodiments of the ophthalmic devices described herein can focus image at the preferred area of the peripheral retina as well as correct for optical errors occurring in the image formed in the area of the peripheral retina due to optical effects such as oblique astigmatism and coma. In some patients without a developed preferred area of peripheral retina, the improvement in the peripheral vision brought about from correcting the optical errors in the image formed at a location of the peripheral retina can help in development of a preferred area of the peripheral retina.

The embodiments described herein are directed to ophthalmic lenses, such as an IOL, and a system and method relating to providing ophthalmic lenses that can improve visual acuity and/or contrast sensitivity when there is a loss of central vision by focusing incident light onto an area on the peripheral retina around the fovea or at a region of the peripheral retina where vision is best. Such ophthalmic lenses can include spheric/aspheric refractive surfaces, refractive structures such as prisms and diffractive structures such as gratings to focus incident light onto a region of the peripheral retina around the fovea.

One aspect of the subject matter described in this disclosure can be implemented in an intraocular lens configured to improve vision for eyes having no or reduced foveal vision. The intraocular lens comprises a first zone having an optical axis which intersects the retina of the eye at a location external to the fovea; and a second zone having an optical axis which intersects the retina of the eye at the fovea, wherein the first zone has a power that is greater than the second zone.

Another aspect of the subject matter described in this disclosure can be implemented in a method for improving vision where there is no or reduced foveal vision using an intraocular lens with at least two zones. The method comprises determining a deflected optical axis which intersects a retina of a user at a preferred retinal locus; modifying a first zone of the intraocular lens to redirect incident light along the deflected optical axis; modifying a second zone of the intraocular lens to direct incident light along an undeflected optical axis which intersects a retina of a user at the fovea; and adjusting a power of the first zone to be greater than a power of the second zone.

One aspect of the subject matter described in this disclosure can be implemented in an intraocular lens configured to improve vision where there is a loss of retinal function (e.g., a loss of foveal vision), the intraocular lens comprising: a redirection element configured to redirect incident light along a deflected optical axis which intersects a retina of a user at a preferred retinal locus. The redirection element comprises a surface with a slope profile that is tailored such that, in use, the intraocular lens: redirects incident light along the deflected optical axis; focuses the incident light at the preferred retinal locus; and reduces optical wavefront errors, wherein the slope profile is tailored to redirect and focus the incoming rays on the preferred retinal locus. The slope profile can be tailored based at least in part on a solution to an analytical equation that is a function of a distance from the IOL vertex to the original focus (l), an index of refraction of the IOL ($n_l$), an index of refraction of the aqueous environment ($n_{aq}$), an angle inside the eye to the preferred retinal locus relative to a back vertex of the IOL ($a_p$), a radial position of the IOL (x), and/or the posterior radius of curvature of the IOL (r), the analytical equation given by the following:

$$\text{slope}(x) = -\cos^{-1}\left(\frac{n_{aq}\cos\alpha - n_l\cos\beta}{\sqrt{n_{aq}^2 + n_l^2 - 2n_{aq}n_l\sin\alpha\sin\beta - 2n_{aq}n_l\cos\alpha\cos\beta}}\right),$$

wherein $$\alpha = \tan^{-1}\left(\frac{l\sin a_p - x}{l\cos a_p - r - \sqrt{r^2 - x^2}}\right),$$

and wherein $$\beta = \sin^{-1}\left(\frac{n_{aq}}{n_l}\sin\left(\tan^{-1}\left(\frac{-x}{l - r - \sqrt{r^2 - x^2}}\right) + \sin^{-1}\left(\frac{x}{r}\right)\right)\right).$$

In some implementations, the slope profile can be tailored based at least in part on an analytical solution to an equation describing an eye of a patient. In some implementations, the slope profile can be tailored based at least in part on simulations performed using ray tracing techniques. In some implementations, the slope profile can be determined analytically using an equation that incorporates an axial length to the preferred retinal locus, an angle of the deflected optical axis relative to an undeflected optical axis, and a radial position of the preferred retinal locus. In various implementations, the slope profile can be tailored using an iterative procedure that adjusts a portion of the slope profile to account for a thickness of the redirection element.

The redirection element can comprise a plurality of zones. Each zone can have a slope profile that is tailored based at least in part on the solution to an equation (e.g., the analytical equation given above). In various implementations, a thickness of the redirection element can be less than or equal to 0.5 mm. In various implementations, a curvature of a posterior surface of the intraocular lens is configured to provide a focused image at the fovea of the retina of the patient. In various implementations, the redirection element can be a separate, additional surface on the intraocular lens. In some implementations, the redirection element can be a ring structure. In some implementations, the redirection element can cover a central portion of the intraocular lens. The central portion can have a diameter that is greater than or equal to 1.5 mm and less than or equal to 4.5 mm. In various implementations, a posterior surface of the intraocular lens can include the redirection element, and an anterior surface of the intraocular lens can include a second redirection element comprising a plurality of zones, each zone having a slope. In some implementations, a posterior surface and/or an anterior surface of the intraocular lens can be toric, aspheric, higher order aspheric, a Zernike surface or some other complex surface. In various implementations, the posterior surface and/or the anterior surface of the IOL can be configured to reduce astigmatism and coma in the focused image produced at the preferred retinal locus. In various implementations, a portion of the IOL can include the redirection element and another portion of the IOL can be devoid of the redirection element. In such implementations, the portion of the IOL including the redirection element can have an optical power that is different from the portion of the IOL that is devoid of the redirection element.

Another aspect of the subject matter described in this disclosure can be implemented in a method for improving vision where there is no or reduced foveal vision using an intraocular lens and a redirection element having a tailored slope profile. The method comprising: determining a deflected optical axis which intersects a retina of a user at a preferred retinal locus; calculating a tailored slope profile for the redirection element, the tailored slope profile comprising a plurality of slope values calculated at a corresponding plurality of points on a surface of the intraocular lens; determining optical aberrations at the preferred retinal locus based at least in part on redirecting light using the redirection element with the tailored slope profile; adjusting the slope profile to account for a thickness of the redirection element; and determining whether a quality of an image produced by the redirection element with the adjusted tailored slope profile is within a targeted range.

One aspect of the subject matter described in this disclosure can be implemented in a method of using an intraocular lens to improve optical quality at a preferred retinal locus, the method comprising: obtaining an axial length along an optical axis from a cornea to a retina; obtaining an axial length along an axis which deviates from the optical axis and intersects the retina at the preferred retinal locus. The method further comprises determining a corneal power based at least in part on measurements of topography of the cornea; estimating an axial position of the intraocular lens wherein the intraocular lens with initial optical properties at the estimated axial position is configured to provide a focused image at a fovea. The method further comprises adjusting the initial optical properties of the intraocular lens to provide adjusted optical properties, the adjusted optical properties based at least in part on the axial length along the optical axis, the axial length along the deviated axis to the preferred retinal locus, and the corneal power, wherein the adjusted optical properties are configured to reduce peripheral errors at the preferred retinal location in relation to the intraocular lens with the initial optical properties.

Another aspect of the subject matter described in this disclosure can be implemented in an ophthalmic device configured to deflect incident light away from the fovea to a desired location of the peripheral retina. The device comprises an optical lens including an anterior optical surface configured to receive the incident light, a posterior optical surface through which incident light exits the optical lens and an axis intersecting the anterior surface and posterior surface, the optical lens being rotationally symmetric about the axis. The device further comprises an optical component disposed adjacent the anterior or the posterior surface of the optical lens, the optical component having a surface with a refractive index profile that is asymmetric about the axis.

One aspect of the subject matter described in this disclosure can be implemented in an ophthalmic device comprising an optical lens including an anterior optical surface configured to receive the incident light, a posterior optical surface through which incident light exits the optical lens and an optical axis intersecting the anterior surface and posterior surface. The device further comprises an optical component disposed adjacent the anterior or the posterior surface of the optical lens, the optical component including a diffractive element, wherein the optical component is configured to deflect incident light away from the fovea to a desired location of the peripheral retina.

One aspect of the subject matter described in this disclosure can be implemented in an optic configured to improve vision for a patient's eye. The optic comprises a surface configured to improve image quality of an image produced by light incident on the patient's eye at an oblique angle with respect to an optical axis intersecting the eye and focused at a peripheral retinal location disposed at a distance from the fovea. The image quality is improved by reducing oblique astigmatism at the peripheral retinal location. The image quality can also be improved by reducing coma at the peripheral retinal location. The optic can be configured to optimize the image at the peripheral retinal location by providing astigmatic correction of at least 0.5 Diopter at the peripheral retinal location. The optic can be configured to optimize the image at the peripheral retinal location by providing at least 0.1 µm of coma correction at the peripheral retinal location for a 6 mm pupil.

The oblique angle can be between about 1 degree and about 25 degrees. The peripheral retinal location can be disposed at an eccentricity of about 1 degree to about 25 degrees with respect to the fovea in the horizontal or the vertical plane. For example, the peripheral retinal location can be disposed at an eccentricity between about 7 degrees and about 13 degrees in the horizontal plane. As another example, the peripheral retinal location can be disposed at an eccentricity between about 1 degree and about 10 degrees in the vertical plane. One surface of the optic can be configured to be a Zernike surface having a radius of curvature between about 5 mm and about 25 mm. The Zernike surface can have a conic constant between about 0 and about −100. The Zernike surface can have an astigmatic coefficient between about 0 µm and about 4 µm. The Zernike surface can have a coma coefficient between about 0 µm and about 2 µm. The Zernike surface can have a spherical aberration coefficient with a value between 0 µm and 4 µm when measured in air with a 3 mm aperture using an optical bench aberrometer. The surface opposite the Zernike surface can be a spherical surface. The optic can include diffractive features, prismatic features, echelletes etc. to further improve the image quality at the peripheral retinal location An image formed by the optic at the peripheral retinal location can have a modulation transfer function (MTF) of at least 0.2 (e.g., at least 0.3, at least 0.4, at least 0.5. at least 0.6, at least 0.7, at least 0.8, at least 0.9 or values there between) for a spatial frequency of 30 cycles/mm for both the tangential and the sagittal foci. An image formed by the IOL at the fovea can have a MTF of at least 0.2 (e.g., at least 0.3, at least 0.4, at least 0.5. at least 0.6, at least 0.7, at least 0.8, at least 0.9 or values there between) for a spatial frequency of 100 cycles/mm for both the tangential and the sagittal foci.

Another aspect of the subject matter disclosed herein includes a method of designing an optic configured to improve vision for a patient's eye. The method comprises determining a first surface profile of the optic, the first surface being a Zernike surface; and determining a second surface profile of the optic, the second surface being spherical. The determined surface profiles are such that the optic has an optical power that reduces optical errors in an image produced at a peripheral retinal location disposed at a distance from the fovea, wherein the image is produced by focusing light incident on the patient's eye at an oblique angle with respect to an optical axis intersecting the patient's eye at the peripheral retinal location. The first and the second surface profiles can be configured to provide at least 0.5 Diopter of astigmatic correction at the peripheral retinal location. The first and the second surface profiles can be configured to provide at least 0.1 µm of coma correction at the peripheral retinal location for a 6 mm pupil.

The optical power of the IOL that reduces optical errors at the peripheral retinal location can be obtained from a measurement of an axial length along an axis which deviates from the optical axis and intersects the retina at the peripheral retinal location. The optical power of the IOL that reduces optical errors at the peripheral retinal location can be obtained from an estimate of an axial length along an axis which deviates from the optical axis and intersects the retina at the peripheral retinal location, the estimate based on measured ocular characteristics of the patient obtained using a diagnostic instrument. The measured ocular characteristics can include axial length along the optical axis, corneal power based at least in part on measurements of topography of the cornea, pre-operative refractive power and other parameters. The image produced at the peripheral retinal location can have reduced peripheral astigmatism and/or coma.

Another aspect of the subject matter disclosed herein can be implemented in a method of selecting an intraocular lens (IOL) configured to be implanted in a patient's eye. The method comprises obtaining at least one characteristic of the patient's eye using a diagnostic instrument; and selecting an IOL having an optical power that reduces optical errors in an image produced at a peripheral retinal location of the patient's eye disposed at a distance from the fovea, wherein the IOL is configured to produce an image by focusing light incident on the patient's eye at an oblique angle with respect to an optical axis intersecting the patient's eye at the peripheral retinal location. The optical power of the IOL is obtained and/or optimized based on the obtained characteristic. A first surface of the IOL can be a Zernike surface and a second surface of the IOL can be a spherical surface. The image can have reduced coma and/or astigmatism. The oblique angle can be between about 1 degree and about 25 degrees. The IOL can be configured such that the image has a modulation transfer function (MTF) of at least 0.3 for a spatial frequency of 30 cycles/mm for both tangential and sagittal foci.

The obtained characteristic can include at least one of axial length along the optical axis of the patient's eye, corneal power based at least in part on measurements of topography of the cornea, an axial length along an axis which deviates from the optical axis and intersects the retina at the peripheral retinal location, a shape of the retina or a measurement of optical errors at the peripheral retinal location. In some implementations, the optical power can be obtained from an estimate of an axial length along an axis which deviates from the optical axis and intersects the retina at the peripheral retinal location. The estimate can be based on the axial length along the optical axis of the patient's eye and corneal power.

At least one of the surfaces of the IOL can include a redirecting element. The redirecting element can have a tailored slope profile as discussed herein. The redirecting element can include a diffractive feature and/or a prismatic feature. The IOL can be configured to provide at least 0.5 Diopter of astigmatic correction at the peripheral retinal location. The IOL can be configured to provide at least 0.1 μm of coma correction at the peripheral retinal location for a 6 mm pupil.

Various implementations disclosed herein are directed towards an intraocular device (e.g, an intraocular lens, an ophthalmic solution, a laser ablation pattern, etc.) that improves visual acuity and contrast sensitivity for patients with central visual field loss, taking into account visual field, distortion or magnification of the image. The device can be configured to improve visual acuity and contrast sensitivity for patients with AMD through correction of the optical errors for the still healthy retina that the patient uses for viewing. The device can be configured to correct peripheral errors of the retina with or without providing added magnification. The device can be configured to correct peripheral errors of the retina either without field loss or in combination with magnification. The device can be configured to include a near vision zone. The device can be configured to include multiple optical zones with add power. In various implementations, wherein the device is configured to focus light incident in a large patch including a plurality of angles of incidence is focused in a relatively small area of the retina such that the image has sufficient contrast sensitivity. In various implementations, light incident from a plurality of angles of incidence are focused by the device as an extended horizontal reading zone above or below the fovea. In various implementations, light incident from a plurality of angles of incidence are focused by the device in an area surrounding the fovea and extending upto the full extent of the peripheral visual field. In various implementations, the device is configured to provide sufficient contrast sensitivity for light focused at the fovea for patients with early stages of macular degeneration.

Various implementations of the device can include a redirection element that is configured to redirect incident light towards a peripheral retinal location. Various implementations of the device can include symmetric lenses surfaces with aspheric surfaces. Various implementations of the device can include asymmetric lenses surfaces with aspheric surfaces. Various implementations of the device can include asymmetric/symmetric lenses surfaces with aspheric surfaces having curvatures such that when implanted in the eye a distance between the anterior surface of the lens and the pupil is between 2 mm and about 4 mm and the image formed at a peripheral retinal location at an eccentricity between 7-13 degrees has an average MTF greater than 0.2 for a spatial frequency of about 30 cycles/mm. The aspheric surfaces in various implementations the device can include higher order aspheric terms. In various implementations, the device can include a symmetric optical element with a first surface and a second surface intersected by an optical axis. The thickness of the device along the optical axis can vary between 0.5 mm and about 2.0 mm. The first and the second surfaces can be aspheric. In various implementations, the aspheric surfaces can include higher order aspheric terms.

In various implementations, the device can be configured as a piggyback lens that can be provided in addition to an existing lens that is configured to provide good foveal vision. The piggyback lens can be symmetric or asymmetric. The piggyback lens can be configured to be implanted in the sulcus or in the capsular bag in front of the existing lens.

In various implementations, the device can be configured as a dual optic intraocular lens having a first lens and a second lens. One or both surfaces of the first and the second lens can be aspheric. In various implementations, one or both surfaces of the first and the second lens can include higher order aspheric terms. In various implementations of the dual optic intraocular lens, the optic proximal to the closer to the cornea can have a high positive power and can be configured to be moved either axially in response to ocular forces to provide accommodation. In various implementations of the device described herein, the refractive power provided by optic can be changed in response to ocular forces. The change in the refractive power can be brought about through axial movement or change in the shape of the optic. Various implementations of the device described herein can include a gradient index lens. One or more surfaces of the optics included in various implementations of the device described herein can be diffractive to provide near vision. The optical zones of various implementations of the device described herein can be split for different retinal eccentricities.

Another aspect of the subject matter disclosed herein includes a power calculation diagnostic procedure that measures corneal topography, eye length, retinal curvature, peripheral eye length, pupil position, capsular position, or any combination thereof in order to determine characteristic of the intraocular lens device that improves visual acuity and contrast sensitivity for patients with central visual field loss.

Implementations of intraocular devices described herein can include one or more optics with a large optical zone. The implementations of intraocular devices described herein are configured to focus obliquely incident light in a location of the peripheral retina at an eccentricity between about 5-25 degrees (e.g., eccentricity of 10 degrees, eccentricity of 15 degrees, eccentricity of 20 degrees, etc.). For patient with a well-developed preferred retinal location (PRL), various implementations of the intraocular device can be configured to focus incident light at the PRL. For patients without a well-developed PRL, the implementations of intraocular device described herein can help in the formation of the PRL.

This disclosure also contemplates the use of diagnostic devices to determine a region of the peripheral retina which provides the best vision, determining the power of the intraocular device at various locations within the region of the peripheral retina and determining an intraocular device that would correct optical errors including defocus, astigmatism, coma, spherical aberration, chromatic aberration (longitudinal and transverse) at the region of the peripheral retina. When determining the intraocular device that would correct optical errors at the region of the peripheral retina, different figures of merit can be used to characterize the optical performance of different configurations of the intraocular device and the intraocular device that provides the best performance can be selected. The different figures of merit can include MTF at spatial frequencies appropriate for the retinal areas, weighting of retinal areas, neural weighting, and weighting of near vision function.

The methods and systems disclosed herein can also be used to customize IOLs based on the geometry of a patient's retina, the extent of retinal degeneration and the geometry and condition of other structures in the patient's eye. Various embodiments described herein can also treat other conditions of the eye such as cataract and correct for presbyopia, myopia and/or astigmatism in addition to improving visual acuity and/or contrast sensitivity of peripheral vision.

The methods and systems described herein to focus incident light at a region of the peripheral retina around the fovea can also be applied to spectacle lenses, contact lenses, or ablation patterns for laser surgeries (e.g., LASIK procedures).

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Example implementations disclosed herein are illustrated in the accompanying schematic drawings, which are for illustrative purposes only.

FIG. 5D-1 and FIG. 5D-2 illustrate regions of peripheral retina where the optic can improve image quality. FIG. 5E graphically illustrates the variation in image quality versus eccentricity for an implementation of an optic configured to improve image quality at a peripheral retinal location and an optic configured to improve image quality at the fovea.

Like reference numbers and designations in the various drawings indicate like elements.

DETAILED DESCRIPTION

It is to be understood that the figures and descriptions have been simplified to illustrate elements that are relevant for a clear understanding of embodiments described herein, while eliminating, for the purpose of clarity, many other elements found in typical lenses, lens systems and lens design methods. Those of ordinary skill in the arts can recognize that other elements and/or steps are desirable and may be used in implementing the embodiments described herein.

The terms "power" or "optical power" are used herein to indicate the ability of a lens, an optic, an optical surface, or at least a portion of an optical surface, to focus incident light for the purpose of forming a real or virtual focal point. Optical power may result from reflection, refraction, diffraction, or some combination thereof and is generally expressed in units of Diopters. One of ordinary skill in the art will appreciate that the optical power of a surface, lens, or optic is generally equal to the refractive index of the medium (n) of the medium that surrounds the surface, lens, or optic divided by the focal length of the surface, lens, or optic, when the focal length is expressed in units of meters.

The angular ranges that are provided for eccentricity of the peripheral retinal location in this disclosure refer to the visual field angle in object space between an object with a corresponding retinal image on the fovea and an object with a corresponding retinal image on a peripheral retinal location.

Figure 1:
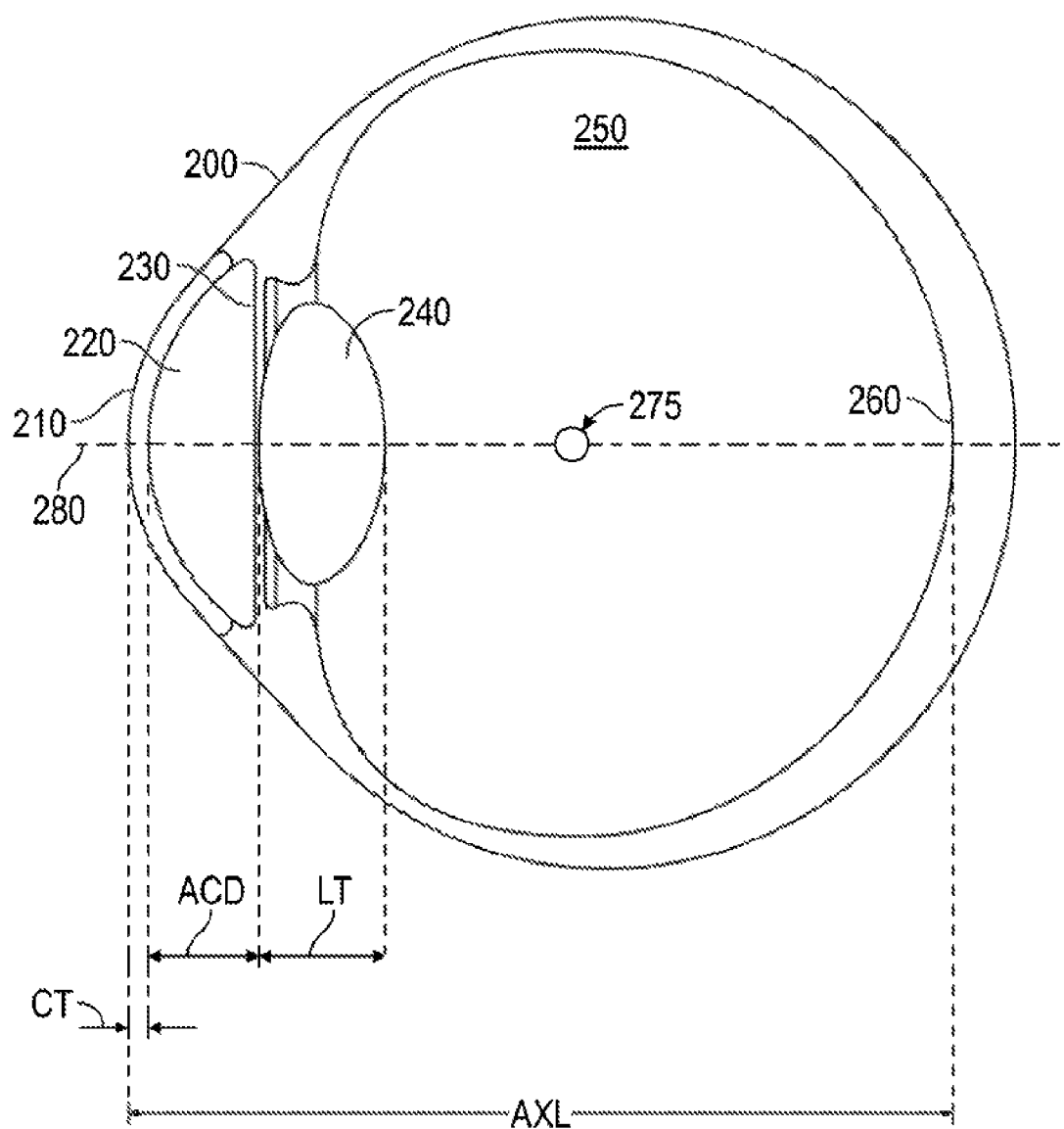
FIG. 1 is a diagram illustrating the relevant structures and distances of the human eye.

FIG. 1 is a schematic drawing of a human eye 200. Light enters the eye from the left of FIG. 1, and passes through the cornea 210, the anterior chamber 220, a pupil defined by the iris 230, and enters lens 240. After passing through the lens 240, light passes through the vitreous chamber 250, and strikes the retina, which detects the light and converts it to a signal transmitted through the optic nerve to the brain (not shown). The eye 200 is intersected by an optical axis 280. The optical axis 280 can correspond to an imaginary line passing through the midpoint of the visual field to the fovea 260. The visual field can refer to the area that is visible to the eye in a given position. The cornea 210 has corneal thickness (CT), which is the distance between the anterior and posterior surfaces of the center of the cornea 210. The corneal center of curvature 275 can coincide with geometric center of the eye 200. The anterior chamber 220 has an anterior chamber depth (ACD), which is the distance between the posterior surface of the cornea 210 and the anterior surface of the lens 240. The lens 240 has lens thickness (LT) which is the distance between the anterior and posterior surfaces of the lens 240. The eye has an axial length (AXL) which is the distance between the center of the anterior surface of the cornea 210 and the fovea 260 of the retina, where the image is focused. The LT and AXL vary in eyes with normal accommodation depending on whether the eye is focused on near or far objects.

The anterior chamber 220 is filled with aqueous humor, and optically communicates through the lens 240 with the vitreous chamber 250. The vitreous chamber 250 is filled with vitreous humor and occupies the largest volume in the eye. The average adult eye has an ACD of about 3.15 mm, although the ACD typically shallows by about 0.01 mm per year. Further, the ACD is dependent on the accommodative state of the lens, i.e., whether the lens 240 is focusing on an object that is near or far.

Figure 2:
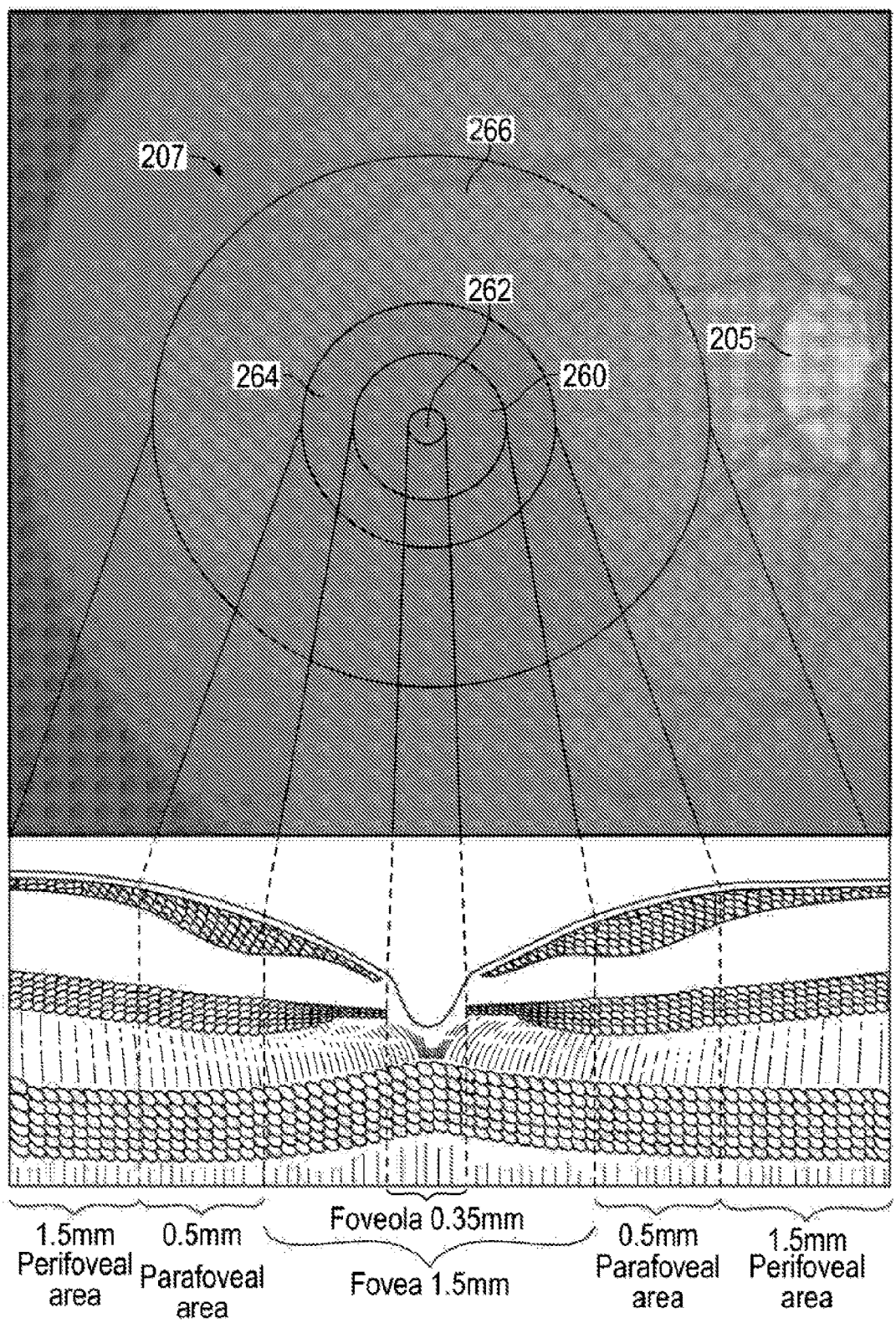
FIG. 2 illustrates different regions of the retina around the fovea.

FIG. 2 illustrates different regions of the retina around the fovea 260. The retina includes a macular region 207. The macular region 207 has two areas: central and peripheral. Light focused on the central area contributes to central vision and light focused on the peripheral area contributes to peripheral vision. The central region is used to view objects with higher visual acuity, and the peripheral region is used for viewing large objects and for capturing information about objects and activities in the periphery, which are useful for activities involving motion and detection.

The macular region 207 is approximately 5.5 mm in diameter. The center of the macular region 207 is approximately 3.5 mm lateral to the edge of the optic disc 205 and approximately 1 mm inferior to the center of the optic disc 205. The shallow depression in the center of the macula region 207 is the fovea 260. The fovea 260 has a horizontal dimension (diameter) of approximately 1.5 mm. The curved wall of the depression gradually slopes to the floor which is referred to as the foveola 262. The diameter of the foveola 262 is approximately 0.35 mm. The annular zone surrounding the fovea 260 can be divided into an inner parafoveal area 264 and an outer perifoveal area 266. The width of the parafoveal area 264 is 0.5 mm and of the perifoveal area 266 is 1.5 mm.

For the general population incident light is focused on the fovea 260. However, in patients suffering from AMD, a scotoma develops in the foveal region which leads to a loss in central vision. Such patients rely on the region of the peripheral retina around the fovea (e.g., the macular region 207) to view objects. For example, patients with AMD can focus incident light on the PRL either by using a magnifying lens that enlarges the image formed on the retina such that a portion of the image overlaps with a portion of the peripheral retina around the fovea or by rotating the eye or the head, thus using eccentric fixation such that light from the object is incident on the eye (e.g. at the cornea) at oblique angles and focused on a portion of the peripheral retina around the fovea. The visual outcome for patients suffering from AMD can be improved if optical errors resulting from oblique incidence of light or coma are corrected. In some AMD patients, a portion of the peripheral retina around the fovea may have has greater visual acuity and contrast sensitivity compared to other portions of the peripheral retina. This portion is referred to as the preferred retinal location (PRL). The visual outcome for such patients may be improved if incident light were focused at the PRL and the ophthalmic solutions corrected for optical errors at the PRL. This is explained in detail below.

Figure 3A:
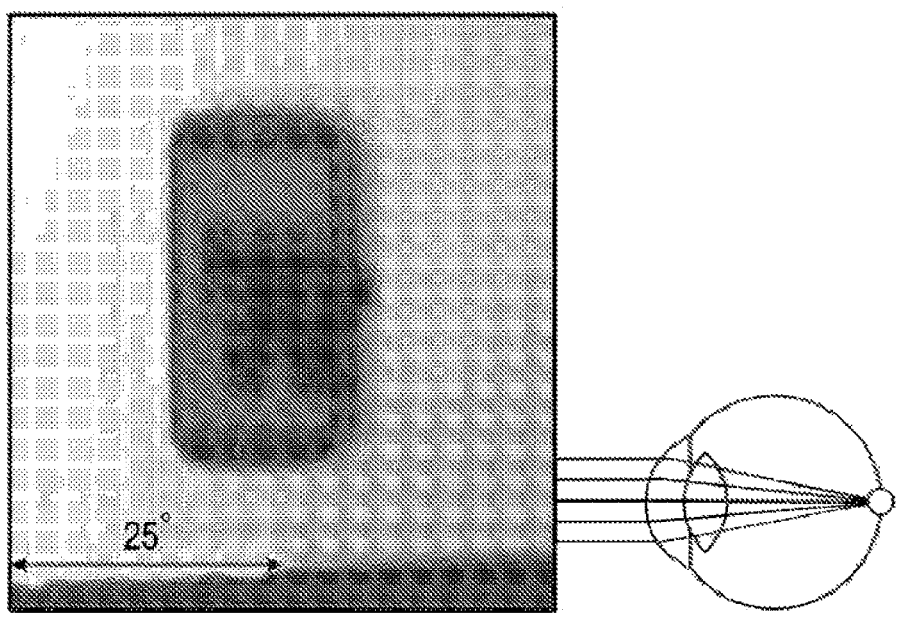
FIG. 3A-3D illustrate simulated vision with a central scotoma along with ophthalmic device embodiments. A ray diagram lies to the right of each simulation.
Figure 3B:
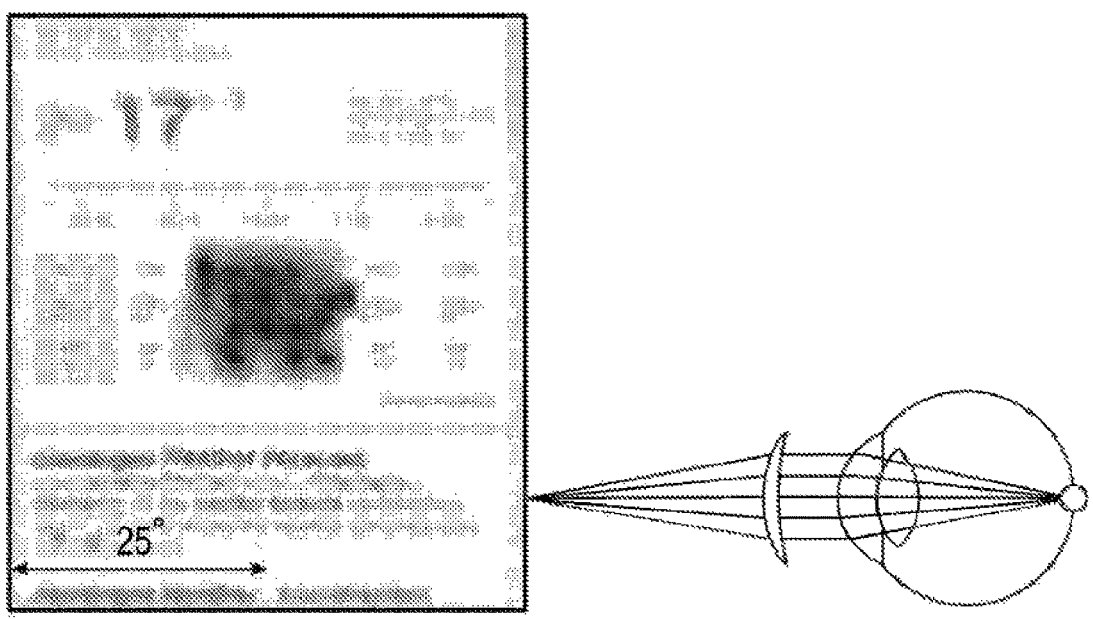
Figure 3C:
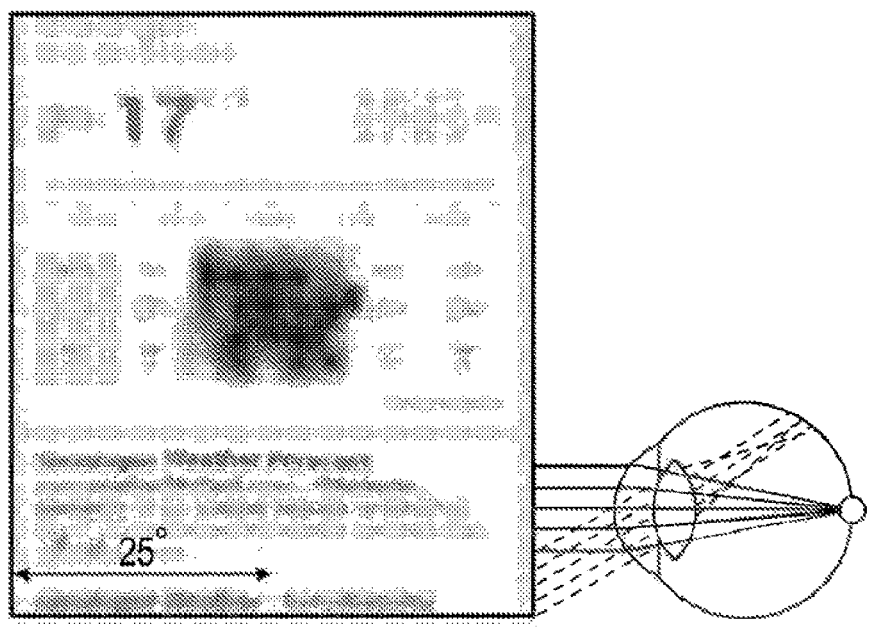

Consider a patient suffering from AMD who desires to view a smart phone at a normal distance (23 cm simulated here). In such a patient, the scotoma will block out the view as seen in FIG. 3A. One solution to improve the visual outcome is to bring the object of interest closer to the eye. This requires a magnifying glass to place the object optically at infinity. FIG. 3B illustrates the simulated view of a smart phone viewed with the aid of a magnifying glass by a patient with a central scotoma. The effect of the magnifying glass is to reduce the object distance and enlarge the size of the image formed on the retina such that it overlaps with a portion of the peripheral retina around the fovea. For the purpose of simulations, it is assumed that the magnifying glass is used and hence the phone is assumed to be at a distance of 7.5 cm. If the patient has cataract in addition to AMD and is implanted with a standard IOL, the peripheral errors will increase. FIG. 3C shows the simulated view of a smart phone viewed by a patient implanted with a standard IOL and who also suffers from AMD. A comparison of FIGS. 3B and 3C illustrates that the smart phone screen appears more blurry when viewed by a patient implanted with a standard IOL due to the increase in peripheral errors.

Figure 3D:
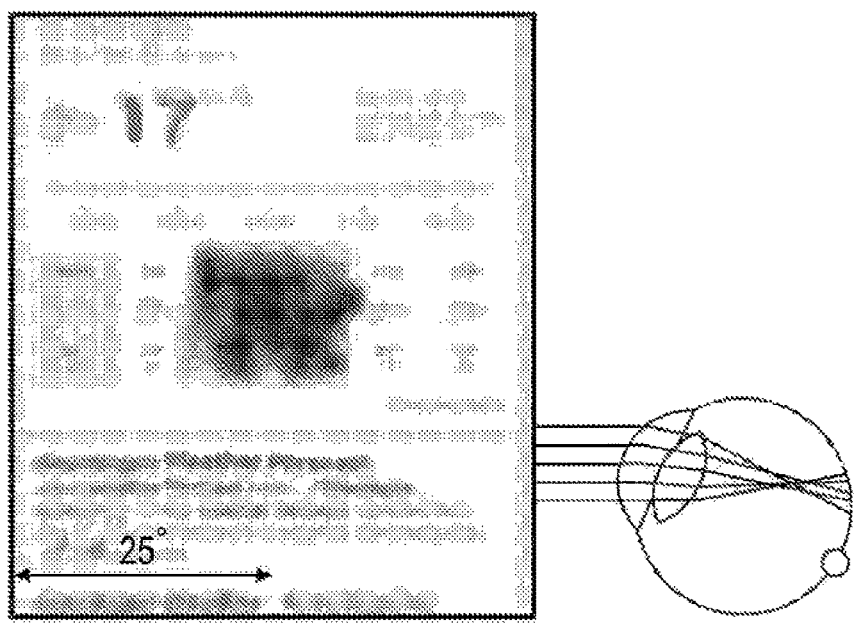

Another solution to improve visual outcome is to utilize eccentric fixation to focus light from a visual interest on to a portion of the peripheral retina. FIG. 3D illustrates a simulated view of a smart phone viewed using eccentric fixation to focus light from the smart phone screen to a position on the peripheral retina located about 12.5 degrees away from the fovea. Since, the image formed at the position on the peripheral retina is formed by light that is obliquely incident on the eye, optical errors arising from the oblique incidence of light may degrade the visual quality. Accordingly, ophthalmic solutions that can correct optical errors arising from oblique incidence of light may benefit AMD patients who rely on eccentric fixation to view objects.

Figure 4A:
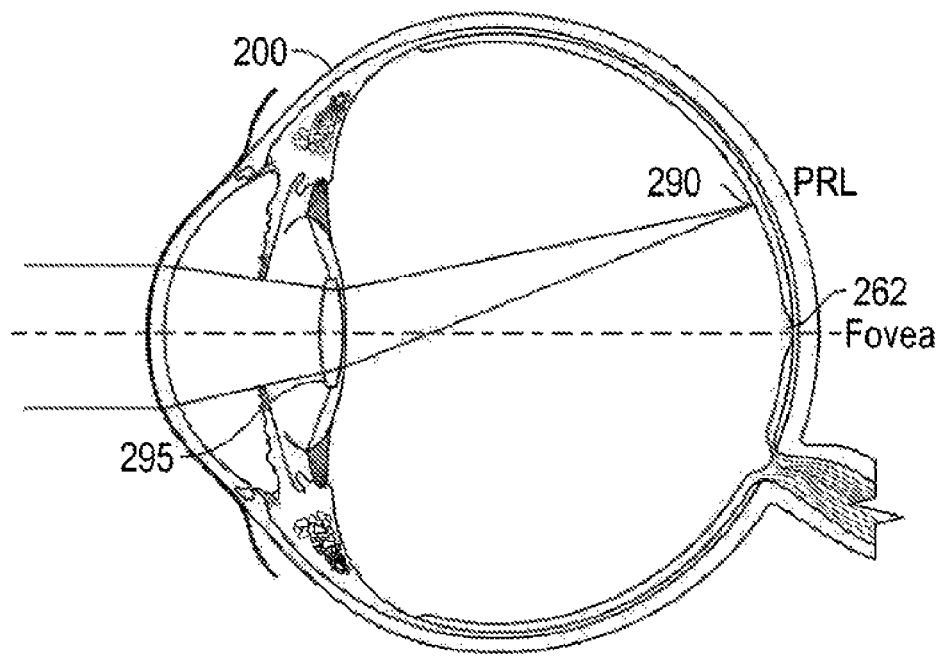
FIG. 4A is a diagram of an eye implanted with an intraocular lens that deflects incident light to a preferred retinal location (PRL).

As discussed above, some patients may have a well-developed PRL and may prefer focusing incident light on the PRL. Such patients can benefit from an IOL that can focus light at the PRL instead of the fovea. FIG. 4A is a diagram of the eye 200 implanted with an IOL 295 that deflects incident light away from the fovea 260 to the PRL 290. For most patients, the PRL 290 is at a distance less than or equal to about 3.0 mm from the fovea 260. Accordingly, the IOL 295 can be configured to deflect incident light by an angle between about 3.0 degrees and up to about 30 degrees such that it is focused at a preferred location within a region at a distance of about 3.0 mm around the fovea 260. The IOL 295 can be customized for a patient by determining the PRL for each patient and then configuring the IOL 295 to deflect incident light such that it is focused at the PRL. The method to find the PRL of any patient is based on Perimetry. One perimetry method to locate the PRL is Goldmann Perimetry. The perimetry method to locate the PRL includes measuring the visual field of a patient. For example, the patient can be asked to fixate on a cross and flashes of lights are presented at various parts in the field and the responses are recorded. From the recorded responses, a map of how sensitive the peripheral retina is can be created. The patient can be trained to consistently use the healthy and more sensitive portions of the retina. The perimetry method can be further enhanced by microperimetry, as used by e.g. the Macular Integrity Assessment (MAIA) device, where the retina is tracked in order to place the stimuli consistently and eye movement are accounted for.

Figure 4B:
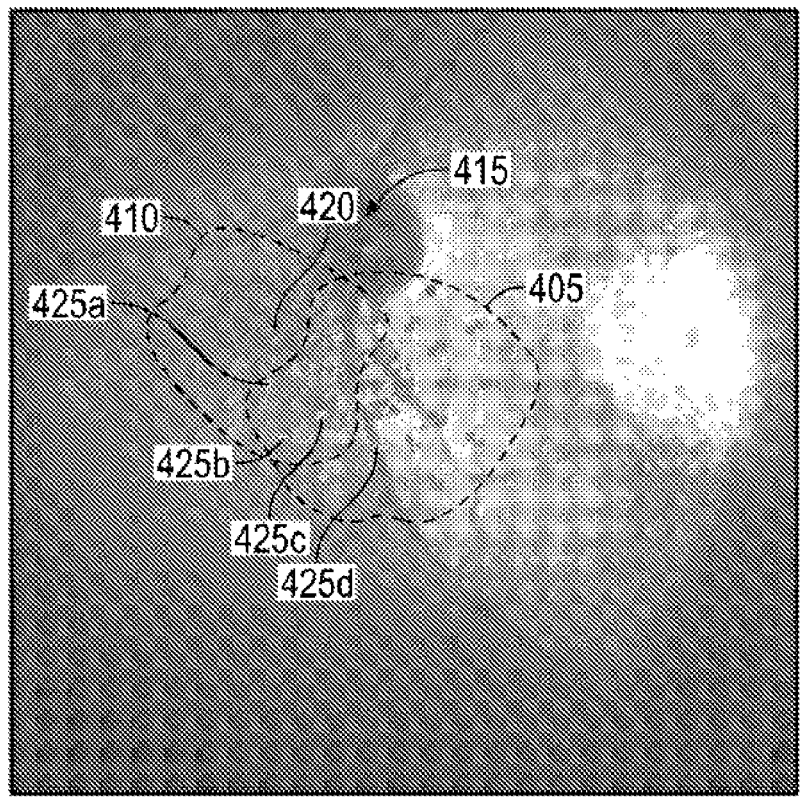
FIG. 4B illustrates an image obtained by a PRL diagnostic device.

The PRL can also be located subjectively, by asking the patient to fixate as they want into an OCT-SLO instrument. The instrument can obtain one or more images of the retina and determining which portions of retina are used more than the other. One method of determining the portions of retina that are used more includes imposing the parts of fixation onto an image of the retina. The OCT-SILO instrument can also be used to obtain normal images of the retina. FIG. 4B illustrates an image obtained using the perimetry method and the fixation method. FIG. 4B shows a photo of the retina with a central scotoma 415. The red-yellow-orange dots in the region marked 405 are the results of the perimetry. Perimetry results indicate that spots closer to the scotoma 415 perform worse that spots farther away from the scotoma 415. The many small teal dots in the region marked 410 are the fixation points, and the lighter teal point 420 is the average of the dots in the region 410. Based on the measurements, the PRL can be located at either point 420 or one some of the yellow points 425a-425d. Accordingly, an IOL 295 can be configured to focus an image at one of the points 420 or 425a-425d. The determination of the PRL for a patient having both cataract and AMD can be made by methods other than the methods described above.

Since, AMD patients rely on their peripheral vision to view objects, their quality of vision can be improved if optical errors in the peripheral vision are identified and corrected. Optical power calculation for an IOL configured for foveal vision is based on measuring eye length and corneal power. However, power calculation for an IOL that focuses objects in an area around a peripheral retinal location offset from the fovea can depend on the curvature of the retina as well as the oblique astigmatism and coma that is associated with the oblique incidence of light in addition to the eye length and the corneal power. Optical power calculation for an IOL that focuses objects in an area around a peripheral retinal location can also depend on the position of the IOL with respect to the iris and an axial length along an axis which deviates from the optical axis and intersects the retina at the peripheral retinal location Methods that are used by an optometrist to measure optical power for spectacle lenses or contact lenses for non AMD patients with good foveal vision are not practical for measuring optical power for ophthalmic solutions (e.g., IOL, spectacle lenses, contact lenses) for peripheral vision. Optometrists use various machines such as autorefractors, as well as a method called subjective refraction wherein the patient reads lines on the wall chart. The response is then used to gauge which trial lenses to put in, and the lenses that give the best results are used. However, such a method is not practical to determine which ophthalmic solution is best for a patient with AMD who relies on peripheral vision to view objects since, the performance estimates are rendered unreliable by the phenomenon of aliasing (a phenomenon which makes striped shirts look wavy on some television sets with poor resolution), the difficulty of fixation and general fatigue associated with orienting the head/eye to focus objects on the peripheral retina. Instead, the methods used to evaluate the optical power of ophthalmic solutions for AMD patients rely on peripheral wavefront sensors to estimate peripheral optical errors. Peripheral wavefront sensors illuminate a small patch of the PRL using lasers and evaluate how the light reflected and coming out of the eye is shaped through an array of micro-lenses. For example, if the light coming out of the eye is converging, the patient is myopic at the PRL.

In various patients suffering from AMD as well as cataract, the natural lens 240 can be removed and replaced with the IOL 295, or implanted in the eye 200 in addition to another IOL placed previously or at the same time as the IOL 295. In some patients suffering from AMD, the IOL 295 can be implanted in the eye 200 in addition to the natural lens 240. In FIG. 4A, the IOL 295 is implanted in the capsular bag. Where possible, the IOL 295 is placed as close to the retina as possible. However, in other implementations, the IOL 295 can be implanted within the capsular bag in front of another IOL or in front of the capsular bag. For example, the IOL 295 can be configured as an iris, sulcus or anterior chamber implant or a corneal implant. By selecting an IOL 295 with appropriate refractive properties, the image quality at the PRL can be improved.

The visual outcome at a peripheral retinal location is poor as compared to the foveal visual due to a decreased density of ganglion cells at the peripheral retinal location and/or optical errors and artifacts that arise due to oblique incidence of light (e.g., oblique astigmatism and coma). Patients with AMD can receive substantial improvement in their vision when optical errors at the peripheral retinal location are corrected. Many of the existing embodiments of IOLs that are configured to improve foveal visual outcome for a patient are not configured to correct for optical aberrations (e.g., coma, oblique astigmatism, etc.) in the image generated at the peripheral retinal location.

It is envisioned that the solutions herein can be applied to any eccentricity. For example, in some patients, a location that is disposed at a small angle from the fovea can be used as the PRL while in some other patients, a location that is disposed at an angle of about 30 degrees from the fovea can be used as the PRL.

Various embodiments of the IOLs disclosed herein are configured to focus light at a location on the peripheral retina to produce good quality images, for example, images produced at the location on the peripheral retina can have a quality that is substantially similar to the quality of images produced at the fovea. The images produced at the location on the peripheral retina by the IOLs disclosed herein can have reduced artifacts from optical effects such as oblique astigmatism, coma or other higher order aberrations. Other embodiments are based on the fact that the location on the peripheral retina is not used in the same way as the fovea. For example, it may be harder to maintain fixation on the PRL, so it may be advantageous to increase the area of the retina where incident light is focused by the IOL in order to have sufficient visual acuity even when fixation is not maintained and/or when the eye is moved linearly as in during reading. As such, the retinal area of interest can cover areas where the refraction differs substantially due to differences e.g. in retinal curvature and oblique astigmatism. Various embodiments of IOLs described herein can be used to direct and/or focus light entering the eye along different directions at different locations of the retina. Simulation results and ray diagrams are used to describe the image forming capabilities of the embodiments described herein.

As used herein, an IOL refers to an optical component that is implanted into the eye of a patient. The IOL comprises an optic, or clear portion, for focusing light, and may also include one or more haptics that are attached to the optic and serve to position the optic in the eye between the pupil and the retina along an optical axis. In various implementations, the haptic can couple the optic to zonular fibers of the eye. The optic has an anterior surface and a posterior surface, each of which can have a particular shape that contributes to the refractive properties of the IOL. The optic can be characterized by a shape factor that depends on the radius of curvature of the anterior and posterior surfaces and the refractive index of the material of the optic. The optic can include cylindrical, aspheric, toric, or surfaces with a slope profile configured to redirect light away from the optical axis and/or a tight focus.

Enhanced Toric Lens to Generate an Image at a Location of the Peripheral Retina for AMD Patients Today, many patients with toric corneas have astigmatism for on-axis vision for light incident along the optical axes 280. This astigmatism can be corrected with a toric IOL, providing good on-axis vision. Patients with AMD could potentially be provided with a toric lens that is configured to focus light incident at oblique angles with respect to the optical axis 280 of the eye of the patient at a location of the peripheral retina, compensating for the oblique astigmatism. The toric lens can be further enhanced to correct higher order aberrations in the image generated at the location of the peripheral retina. For example, the enhanced toric lens can be configured to correct coma at the location of the peripheral retina.

Figure 5A:
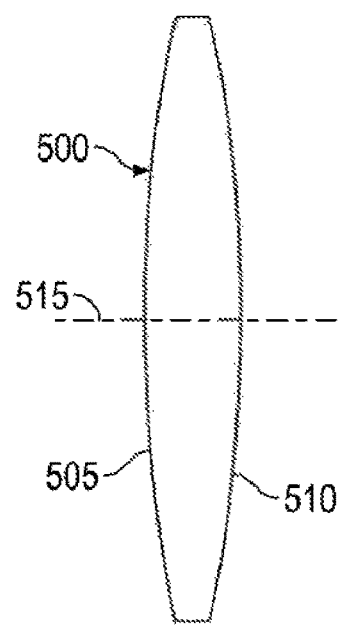
FIG. 5A illustrates an implementation of an optic including at least one aspheric surface that can improve the visual outcome for a patient with AMD.

FIG. 5A illustrates an implementation of an optic 500 that is included in a toric lens. The optic 500 has a first surface 505 and a second surface 510. An optical axis 515 passes through the geometric center of the optic 500 and joins the center of curvatures of the first and second surfaces. The optic 500 illustrated in FIG. 5A is asymmetric about the optical axis 515 such that the image quality in a particular location with respect to the optical axis is better than the image quality at a different location. In various implementations, the optic 500 in conjunction with a toric cornea of the patient can provide uniform image quality about the optical axis 515.

The optic 500 can be included in an intraocular lens (IOL) that can be implanted in the eye of a patient. For example, the optic 500 can be included in a toric IOL that is configured to be inserted between the pupil/iris of the patient and the capsular bag (e.g., in the sulcus of the eye). As another example, the optic 500 can be included in a toric IOL that is configured to be implanted in the capsular bag of the patient's eye. The toric IOL including the optic 500 can be implanted in the patient's eye such that the optical axis 515 of the optic 500 is coincident with the optical axis 280 of the patient's eye. The toric IOL including the optic 500 can be implanted in the patient's eye such that the optical axis 515 of the optic 500 is offset and/or tilted with respect to the optical axis 280 of the patient's eye. When implanted, the first surface 505 can face the cornea of the patient's eye and the second surface 510 can face the retina. Accordingly, in various implementations, the first surface 505 can be referred to as the anterior surface and the second surface 510 can be referred to as the posterior surface. The thickness of the optic 500 along the optical axis 515 can be less than 1.5 mm. For example, the thickness of the optic along the optical axis can vary between about 0.25 mm and about 0.4 mm, about 0.3 mm and about 0.5 mm, about 0.4 mm and about 0.6 mm, about 0.5 mm and about 0.7 mm, about 0.6 mm and about 0.8 mm, about 0.7 mm and about 0.9 mm, about 0.9 mm and about 1.0 mm, about 1.0 mm and about 1.2 mm, or values therebetween.

The first surface 505 and/or the second surface 510 can be spheric, aspheric, biconic, conic, toric, etc. The first surface 505 and/or the second surface 510 can be described mathematically by a polynomial function in either Cartesian or polar coordinates. For example, the first surface 505 and/or the second surface 510 can be described mathematically by equation (1) below:

$$z = \frac{cr^2}{1 + \sqrt{1-(1+k)c^2r^2}} + \sum_{i=0}^{N} \alpha_i r^{2i} \quad (1)$$

where z is the sag of the surface, c is the curvature of the surface, r the radial distance from the optical axis 515, k the conic constant and α the aspheric coefficients. In various implementations, the surface sag (z) of the first surface 505 and/or the second surface 510 can include upto eighth order aspheric terms. In some implementations, the surface sag (z) of the first surface 505 and/or the second surface 510 can include less than eighth order (e.g., 0, 2, 4, 6) or greater than eighth order (e.g., 10 or 12) aspheric terms.

As another example, the first surface 505 and/or the second surface 510 can be described mathematically by equation (2) below:

$$z = \frac{cr^2}{1 + \sqrt{1-(1+k)c^2r^2}} + \sum_{i=1}^{8} \alpha_i r^{2i} + \sum_{i=1}^{N} A_i Z_i(\rho, \phi) \quad (2)$$

where z is the sag of the surface, c is the curvature of the surface, r the radial distance from the optical axis 515, k the conic constant, α the aspheric coefficients, and A are the Zernike coefficients and Z are the Zernike polynomials. Zernike coefficients A5 and A6 correspond to the astigmatic terms and Zernike polynomial numbers A7 and A8 order correspond to the coma term. As discussed above, the surface sag (z) of the first surface 505 and/or the second surface 510 can include up to eighth order aspheric terms, less than eighth order (e.g., 0, 2, 4, or 6) aspheric terms or greater than eighth order (e.g., 10 or 12) aspheric terms. Alternately, the first surface 505 and/or the second surface 510 can be described by up to 34 Zernike polynomial coefficients. In some implementations, the first surface 505 and/or the second surface 510 can be described by less than 34 Zernike coefficients. In some implementations, the first surface 505 and/or the second surface 510 can be described by more than 34 Zernike coefficients. Additionally, the first/and or second surface can be described as a combination of these aspheric and Zernike coefficients. Lenses including aspheric surfaces and other complex surfaces are also described in U.S. application Ser. No. 14/644,082, filed concurrently herewith on Mar. 10, 2015, titled "INTRAOCULAR LENS THAT IMPROVES OVERALL VISION WHERE THERE IS A LOCAL LOSS OF RETINAL FUNCTION," which is incorporated by reference herein in its entirety. Additional implementations of toric lenses are also described in U.S. application Ser. No. 14/644, 082, filed concurrently herewith on Mar. 10, 2015, titled "INTRAOCULAR LENS THAT IMPROVES OVERALL VISION WHERE THERE IS A LOCAL LOSS OF RETINAL FUNCTION," which is incorporated by reference herein in its entirety.

Figure 5B:
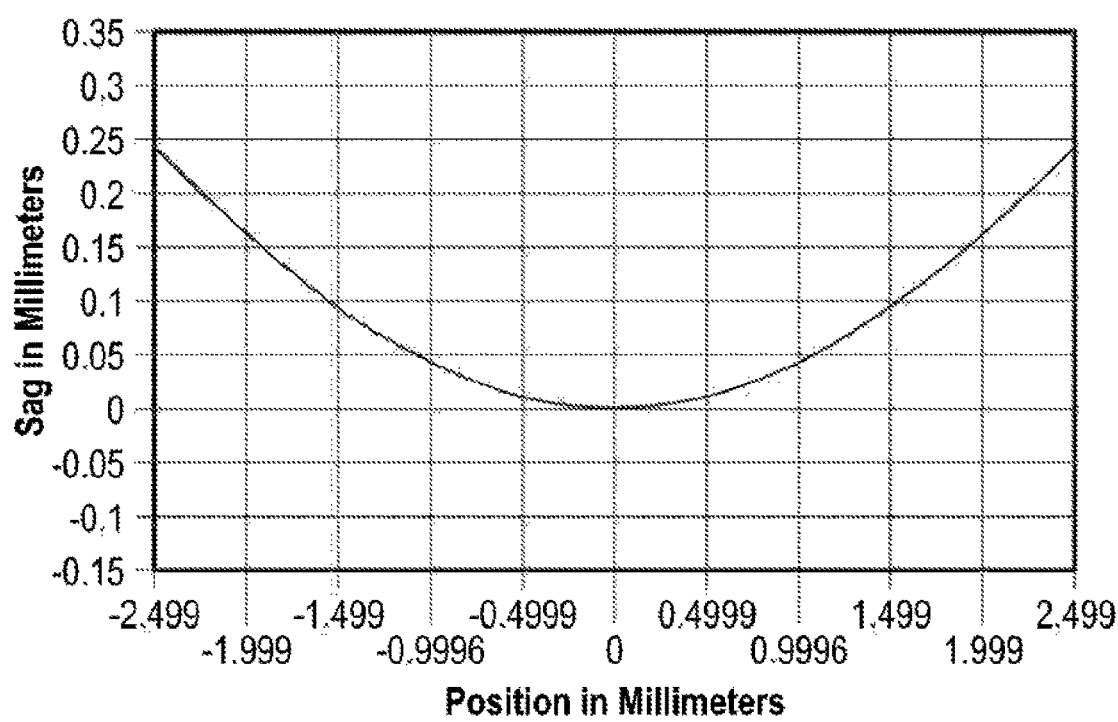
FIG. 5B illustrates the surface profile of the aspheric surface of the lens illustrated in FIG. 5A in a first meridian.
Figure 5C:
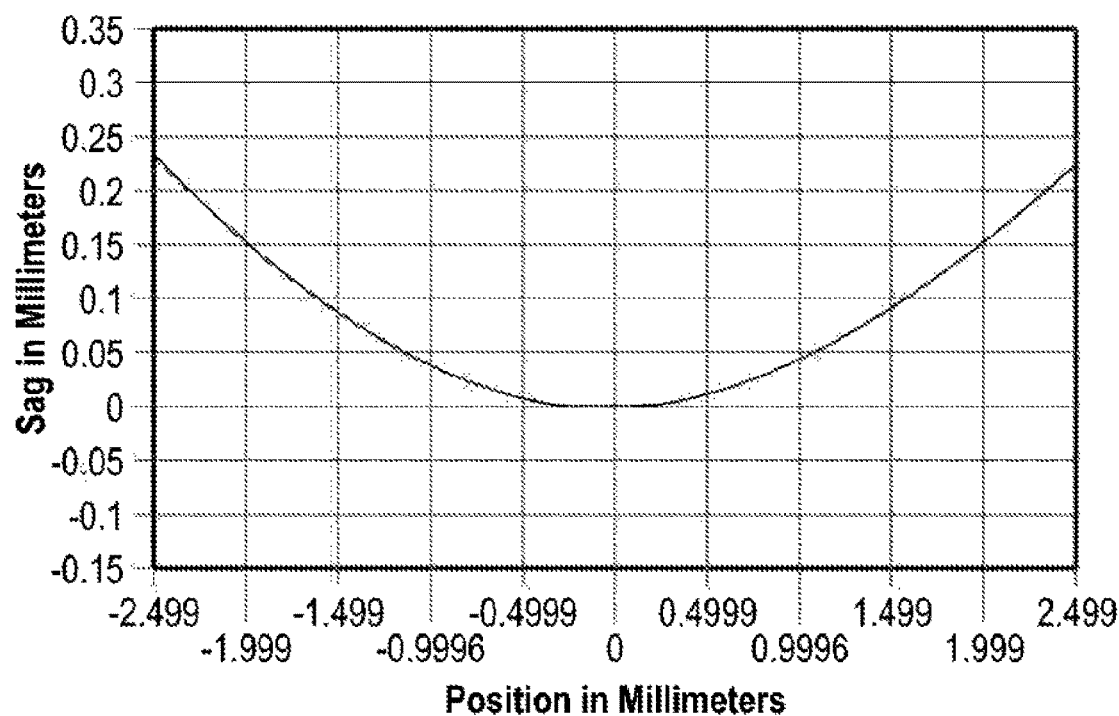
FIG. 5C illustrates the surface profile of the aspheric surface of the lens illustrated in FIG. 5A in a second meridian.

The surface sag of the first surface 505 and/or the second surface 510 can be varied by selecting different values of the curvature, conic constant, and other parameters in equations (1) or (2). In various implementations, the surface sag of the first surface 505 and/or the second surface 510 can be described by other polynomial equations different from equation (1) and equation (2) including at least a radius of curvature, a conic constant, an astigmatic term and a coma term. For example, in the illustrated implementation of the optic 500, the first surface 505 is a Zernike surface, where the surface sag of the first surface can be expressed mathematically using different Zernike terms including the fifth and sixth Zernike coefficients which are referred to as the astigmatic terms and the seventh and eighth Zernike coefficients which are referred to as coma terms. FIG. 5B illustrates the surface sag of the first surface 505 in a first meridian that is oriented horizontally with respect to the optical axis 515 also referred to as the meridian oriented at 0 degrees. FIG. 5C illustrates the surface sag of the first surface 505 in a second meridian that is oriented vertically with respect to the optical axis 515 also referred to as the meridian oriented at 90 degrees. The second surface 510 in the illustrated implementation is spherical.

Configuring the optic 500 to have one Zernike surface and one spheric surface as discussed above can provide some manufacturing benefits. For example, having only one surface configured as an aspheric reduces the number of surface parameters that have to be taken into account in the manufacturing process. Accordingly, an implementation of an optic with one aspheric surface and one spherical surface can be simpler to manufacure as well as easier to inspect and validate than an optic with two aspheric surfaces. In various implementations, diffractive features, prismatic features or echelletes can be disposed on the first surface 505 and/or the second surface of optic 500. In implementations wherein one surface is spherical, the diffractive features, prismatic features or echelletes can be disposed on the spherical surface. In various implementations, a portion of the first surface 505 and/or the second surface of optic 500 can include redirecting elements similar to the prismatic features and/or diffractive features described in U.S. Provisional Application No. 61/950,757, filed on Mar. 10, 2014, titled "INTRAOCULAR LENS THAT IMPROVES OVERALL VISION WHERE THERE IS A LOSS OF CENTRAL VISION," which is incorporated by reference herein in its entirety. The redirecting elements can be configured to redirect light incident on the eye along the optical axis and/or at an angle to the optical axis to one or more locations on the retina.

Depending on the patient's refractive needs, the first surface 505 and/or the second surface 510 of the optic 500 can be convex or concave. For example, in the illustrated implementation, both the first surface 505 and the second surface 510 are convex. However, in other implementations, the first surface 505 can be concave and/or the second surface 510 can be concave. The shape and curvature of the first surface 505 and/or second surface 510 can be selected based on the patient's visual requirements as well the patient's ocular characteristics.

In various implementations, the optic 500 can be configured such that the refractive properties of the optic 500 can be changed in response to the eye's natural process of accommodation. For example, the optic 500 can comprise a deformable material that can compress or expand in response to ocular forces applied by the capsular bag and/or the ciliary muscles. For example, the optic 500 can be configured to change their shape in response to ocular forces in the range between about 1 gram to about 10 grams, 5 to 10 grams, 1 to 5 grams, about 1 to 3 grams or values therebetween to provide an optical power change between about 0.5 Diopters and about 6.0 Diopters. In various implementations, the optic 500 can comprise materials such as acrylic, silicone, polymethylmethacrylate (PMMA), block copolymers of styrene-ethylene-butylene-styrene (C-FLEX) or other styrene-base copolymers, polyvinyl alcohol (PVA), polystyrenes, polyurethanes, hydrogels, etc. The optic 500 can comprise structures and materials that are described in U.S. Publication No. 2013/0013060 which is incorporated by reference herein in its entirety.

As discussed above, the optic 500 can be incorporated in an IOL that is provided with a haptic that holds the IOL in place when implanted in the eye. The haptic can comprise a biocompatible material that is suitable to engage the capsular bag of the eye, the iris 230, the sulcus and/or the ciliary muscles of the eye. For example, the haptic can comprise materials such as acrylic, silicone, polymethylmethacrylate (PMMA), block copolymers of styrene-ethylene-butylene-styrene (C-FLEX) or other styrene-base copolymers, polyvinyl alcohol (PVA), polystyrene, polyurethanes, hydrogels, etc. In various implementations, the haptic can include a one or more arms that are coupled to the optic 500. For example, the haptic can be configured to have a structure similar to the structure of the biasing elements disclosed in U.S. Publication No. 2013/0013060 which is incorporated by reference herein in its entirety. In various implementations, the haptic can include one or more arms that protrude into the optic 500. In various implementations, the haptic can be configured to move the optic 500 along the optical axis of the eye in response to ocular forces applied by the capsular bag and/or the ciliary muscles. For example, the haptic can include one or more hinges to facilitate axial movement of the optic. As another example, the haptic can include springs or be configured to be spring-like to effect movement of the optic 500. In this manner, the axial position of the optic 500 can be varied in response to ocular forces to provide vision over a wide range of distances. An IOL that is configured to change the axial position of the optic and/or shape and size of the optic in response to ocular forces applied by the capsular bag and/or ciliary muscles can be referred to as an accommodating lens.

The optic 500 is configured such that light incident on the cornea at oblique angles to the optical axis 280 of the eye is focused on a location of the peripheral retina away from the fovea. The light can be incident in the vertical field of view or the horizontal field of view. For example, the optic 500 can be configured to focus light incident at oblique angles between about 5 degrees and about 30 degrees with respect to the optical axis 280 of the eye, between about 10 degrees and about 25 degrees with respect to the optical axis 280 of the eye, between about 15 degrees and about 20 degrees with respect to the optical axis 280 of the eye, or there between at a location on the peripheral retina away from the fovea.

The optic 500 can also be configured such that light incident on cornea along a direction parallel to the optical axis is focused on the fovea for those patients with early AMD who still have some foveal vision. For example, some patients may have parts of the fovea covered by a scotoma instead of a central scotoma. Such patients may have some residual foveal vision and can benefit from incident light being focused at the fovea by the optic 500. Additionally, the optic 500 can also be configured to accommodate to focus objects located at different distances on to the retina (e.g., at a location on the periphery of the retina and/or the fovea) in response to ocular forces exerted by the capsular bag and/or ciliary muscles.

The implementations of the optic 500 described in this disclosure can be configured to correct lower order errors (e.g. sphere and cylinder), higher order aberrations (e.g., coma, trefoil) or both resulting from the oblique incidence of light in the image formed at a location of the peripheral retina. The characteristic of the first surface 505 and/or the second surface 510 of the optic 500, the thickness of the optic 500, etc. can be designed such that the optic 500 can focus light incident at a plurality of oblique angles (e.g., between about −25 degree and about +25 degrees with respect to the optical axis of the eye) in an area around a location on the peripheral retina spaced away from the fovea with sufficient visual contrast. This is explained in further detail below with respect to FIG. 5D.

Figure 5D:
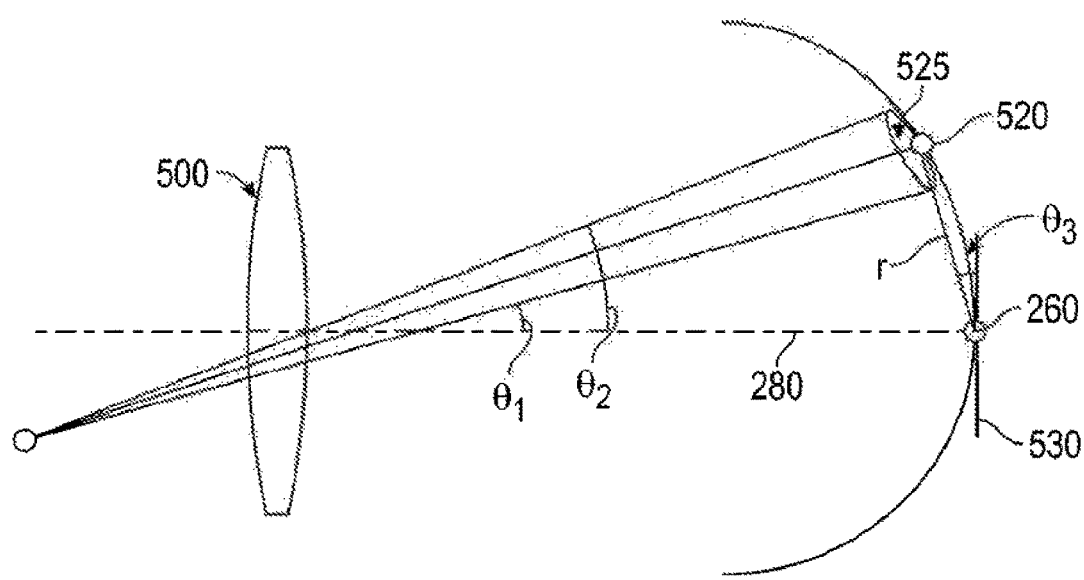
FIG. 5D shows a cross-section view of an eye with a central scotoma at the fovea and implanted with an implementation of an IOL including the optic illustrated in FIG. 5A.

FIG. 5D shows a cross-section view of an eye with a central scotoma at the fovea 260 and implanted with an implementation of an IOL including the optic 500 illustrated in FIG. 5A. Light from an object is incident in a range of oblique angles between $\theta_1$ and $\theta_2$ with respect to the optical axis 280 and are focused by the optic 500 in an area 525 disposed around a location 520 on the peripheral retina disposed away from the fovea 260. For most patients $\theta_1$ can be between 3 degrees and 5 degrees and $\theta_2$ can be between 10 degrees and 35 degrees. The location 520 can be located at a distance r from the fovea 260 along a direction that makes an angle $\theta_3$ with respect to a tangential line 530 intersecting the retina at the fovea 260 and lying in the tangential plane. Although, not shown in FIG. 5D, the location 520 can be located at a distance r from the fovea 260 along a direction that makes an angle $\theta_4$ with respect to a tangential line (not shown) intersecting the retina at the fovea 260 and lying in the sagittal plane. The angles $\theta_3$ and $\theta_4$ can have a value greater than or equal to 0 degrees and less than 30 degrees. The distance r can have a value between about 0.5 mm and about 4 mm.

The area 525 can be described as the region between a first region which is the base of a cone having a semi angle of $\theta_1$ degrees with respect to the optical axis 280 and a second region which is the base of a cone having a semi angle of about $\theta_2$ degrees with respect to the optical axis 280. Accordingly, the angular width of the area 525 is given by $(\theta_2-\theta_1)$. For most patients, the angular width of the area 525 can be between about 5 degrees and about 30 degrees. Without any loss of generality, the area 525 can include locations that are within about 2-5 mm from the fovea 260. The area 525 can have an angular extent $\Delta\theta_{1h}$ in the horizontal plane and an angular extent $\Delta\theta_{1v}$ in the vertical plane. In various implementations, the angular extent $\Delta\theta_{1v}$ can be zero or substantially small such that the area 525 is a horizontal line above or below the fovea 260. Alternately, the angular extent $\Delta\theta_{1h}$ can be zero or substantially small such that the area 525 is a vertical line to the left or the right of the fovea 260. In some embodiments, the angular extent $\Delta\theta_{1v}$ and the angular extent $\Delta\theta_{1h}$ can be equal such that the area 525 is circular. In some other implantations, the angular extent $\Delta\theta_{1h}$ and the angular extent $\Delta\theta_{1v}$ can be unequal such that the area 525 is elliptical. In various implementations, the angular extent $\Delta\theta_{1v}$ and the angular extent $\Delta\theta_{1h}$ have values such that the area 525 includes the fovea 260. However, in other implementations, the angular extent $\Delta\theta_{1v}$ and the angular extent $\Delta\theta_{1h}$ can have values such that the area 525 does not include the fovea 260.

Generally, patients with AMD experience greater improvement in their vision when refractive errors arising from the oblique astigmatism and coma are corrected for image formed at a location in the peripheral retina than patients without AMD at similar retinal eccentricities. Accordingly, the characteristics of the first surface 505, the second surface 510, the thickness of the optic 500 and its orientation when implanted in the eye can be adjusted such that the refractive errors due to relative peripheral defocus, oblique astigmatism and coma in an image produced at a location of the peripheral retina by the optic 500 are reduced. The improvement in the image quality produced by the optic 500 arises partly from the correction of peripheral errors and partly from the correction of peripheral coma. Since, both peripheral coma and peripheral astigmatism depend on the angle of incidence with respect to the optical axis, they are linked. Therefore, each cylinder comes with a corresponding fixed amount of coma correction. For example, the optic 500 can have a spherical power which depends on corneal power and eye length and astigmatism which depends on corneal astigmatism. The optic 500 can also include an astigmatic correction that depends on oblique astigmatism, and coma. The oblique astigmatism and coma can be linked since they both depend on the oblique angle of incidence. For example, if the optic 500 is configured to provide 1.0 Diopter of oblique astigmatism correction, then it will simultaneously provide 0.1 micrometer of coma correction. As another example, if the optic 500 is configured to provide 4.0 Diopter of oblique astigmatism correction, then it will simultaneously provide 0.2 micrometer of coma correction. Oblique astigmatism scales quadratically with field angle while coma scales linearly, so coma can be predicted from the value of the oblique astigmatism. The optic 500 can also be configured to provide good visual quality at the fovea 260 for those patients who have early stage AMD.

Additionally, the optic 500 can also be configured to provide good image quality at the fovea for those patients who have early stage AMD. In contrast to optics and IOLs that are configured to improve image quality at the fovea, the optic 500 is configured to improve image quality in a region of the peripheral retina that is offset from the fovea. For example, the optic 500 can be configured to improve image quality in an annular zone surrounding the fovea 260 as shown in FIG. 5D-1. The annular zone can include an area 545 between an inner periphery 535 surrounding the fovea and an outer periphery 540 surrounding the fovea 260. The inner periphery 535 can include retinal locations at an eccentricity between about 1 degree and about 10 degrees. Without any loss of generality, as used herein, the term eccentricity refers to the angle between a normal to the retina at the location of interest and the optical axis of the eye which intersects the retina at the fovea. Accordingly, the fovea is considered to have an eccentricity of about 0 degrees. The outer periphery 540 can include retinal locations at an eccentricity between about 3 degrees and about 25 degrees. Although in FIG. 5D-1 the optic 500 is not configured to improve image quality in the foveal region, in various implementations, the area 545 in which the optic 500 is configured to improve image quality can extend to the foveal region and include the fovea 260 for patient who have residual foveal vision. In such implementations, the optic 500 can be configured to provide good image quality at the fovea as well as at peripheral retinal locations at an eccentricity between about 1 degree and about 25 degrees. In various implementations, the region 545 can be symmetric about the fovea 260. In some implementations, a projection of the region 545 on a plane tangential to the retina at the fovea 260 can be circular, oval or any other shape.

As another example, the optic 500 can be configured to improve image quality in a region 548 surrounding a preferred retinal location (e.g., location 520 as shown in FIG. 5D) offset from the fovea as shown in FIG. 5D-2. The preferred retinal location can be located at an eccentricity between about 1 degree and about 25 degrees. The region 548 surrounding the preferred retinal location 520 can include retinal locations at an eccentricity between about 1 degree and about 25 degrees.

The image quality at the region of the peripheral retina can be improved by optimizing the image quality produced by the optic 500 such that optical errors (e.g., peripheral astigmatism, coma, trefoil, etc.) are reduced at the peripheral retinal region. For example, the image quality at the peripheral retinal region can be increased by correcting optical errors at the peripheral retinal region, correcting for corneal astigmatism at the peripheral retinal region, reducing optical errors resulting from oblique astigmatism at the peripheral retinal region, reducing coma at the peripheral retinal region and/or reducing other higher order aberrations at the peripheral retinal region.

The improvement in the image quality at the peripheral retinal region provided by the optic 500 can be measured using different figures of merit discussed below. One figure of merit that can be used to measured image quality is the modulus of optical transfer function (MTF) at one or more spatial frequencies which provides a measure of contrast sensitivity or sharpness. The MTF for the optic 500 is calculated for both sagittal rays and tangential rays originating from an object disposed with respect to the intersection of the optic and the optical axis of the eye. Accordingly, two MTF curves are calculated one for sagittal rays and the other for tangential rays. For an image to have good quality and sufficient contrast sensitivity, the MTF for both the tangential rays and the sagittal rays should be above a threshold. The MTF is calculated for various off-axis positions of the object represented by coordinates along the x-direction and the y-direction in a Cartesian coordinate system in which the point of intersection of the optic and the optical axis of the eye is disposed at the origin of the Cartesian coordinate system and the optical axis is along the z-direction. In various implementations, the point of intersection of the optic and the optical axis of the eye can coincide with the geometric of the optic and/or the geometric center of a surface of the optic.

The MTF of the optic 500 refers to how much of the contrast ratio in the object is preserved when the object is imaged by the optic. A MTF of 1.0 indicates that the optic does not degrade the contrast ratio of the object and MTF of 0 indicates that the contrast ratio is degraded such that adjacent lines in the object cannot be resolved when the object is imaged by the optic. Accordingly, the MTF is a measure of contrast sensitivity or sharpness. Another figure of merit can include average MTF for a range of retinal locations and eccentricities, either close to a single PRL or for multiple PRLs for the patient, and with spatial frequencies chosen to match the retinal sampling. Other figures of merit can include area under the MTF curve for different spatial frequencies, average MTF for a range of spatial frequencies or combinations of the figures of merit listed here.

An optic (e.g., the optic 500) that is configured to improve image quality in the peripheral retinal region can provide a MTF greater than a threshold value ($MTF_{THR}$) at one or more spatial frequencies for an image produced at the desired peripheral retinal region. Similarly, an optic that is configured to improve image quality in the foveal region can provide a MTF greater than a threshold value ($MTF_{THR}$) at one or more spatial frequencies for an image produced at the foveal region. The threshold value ($MTF_{THR}$) can be subjective and be determined based on the patient's needs and ophthalmic condition. For example, some patients may be satisfied with an image quality having a MTF greater than 0.1 for spatial frequencies between 10 cycles/mm and 50 cycles/mm. Some other patients may desire a MTF greater than 0.5 for spatial frequencies between 1 cycle/mm and 100 cycles/mm. Accordingly, the threshold MTF value ($MTF_{THR}$) can vary depending on the lens design and the patient's needs. The increase in MTF value can be correlated with an improvement in the patient's ability to read various lines in an eye chart. For example, without any loss of generality, an increase in MTF from 0.7 to 0.8 can correspond to about 15% contrast sensitivity improvement, or 1 line of visual acuity (VA). Similarly, an increase in MTF from 0.7 to 0.9 can correspond to about 30% increase in contrast sensitivity or 2 lines VA.

FIG. 5E which shows the variation in image quality versus eccentricity for an implementation of an optic configured to improve image quality at a peripheral retinal region and an optic configured to improve image quality at the fovea region. Curve 550 shows the variation of MTF versus eccentricity for an optic configured to improve image quality at a peripheral retinal region while curve 555 shows the variation of MTF versus eccentricity for an optic configured to improve image quality at the foveal region. As shown in FIG. 5E the optic configured to improve image quality at a peripheral retinal region provides a MTF greater than a threshold value ($MTF_{THR}$) at one or more spatial frequencies at an eccentricity between 1 degree and 25 degrees and −1 degree and −25 degrees such that an image produced in the peripheral retinal region at an eccentricity between 1 degree and 25 degrees and −1 degree and −25 degrees has sufficient contrast sensitivity. In various implementations, the optic may be configured to improve image quality at a peripheral retinal region at the expense of foveal vision. For example, the optic configured to improve image quality at a peripheral retinal region may provide a MTF less than the threshold value ($MTF_{THR}$) in the foveal region (e.g., at an eccentricity between −1 degree and 1 degree). In contrast, an optic configured to improve foveal vision will provide an MTF greater than the threshold value ($MTF_{THR}$) for an image produced in the foveal region. In some implementations, the optic configured to improve image quality at a peripheral retinal region may also be configured to provide a MTF value greater than the threshold value ($MTF_{THR}$) at the foveal region as shown by curve 560.

One way to configure the optic 500 to reduce optical errors at a peripheral retinal region is to determine the surface profiles of the optic 500 that reduce optical errors due to oblique astigmatism and coma at the peripheral retinal region when light incident on the eye obliquely with respect to the optical axis 280 is focused by the IOL system 500 at the peripheral retinal region. Using a lens designing system various surface characteristics of the first and/or second surface 505 and 510 of the optic 500 can be determined that reduce optical errors at a peripheral location of the retina. The various surface characteristics can include curvatures, surface sags, radius of curvatures, conic constant, axial thickness, area of the optical zone, diffractive features, echelletes and/or prismatic features provided with the optic, etc. The surface characteristics can be determined using an eye model that is based on average population statistics. Alternately, the surface characteristics can be determined by using an eye model that is specific to each patient and constructed using a patient's individual ocular characteristics. Some of the ocular characteristics that can be taken into consideration when determining the characteristics of the surfaces of the optic 500 can include corneal radius of curvature and asphericity, axial length, retinal curvatures, anterior chamber depth, expected lens position, location of image on the peripheral retina, size of the scotoma, optical and physical characteristics of the existing lens, peripheral aberrations, etc. Depending on the patient's needs, the first and/or the second surface 505, 510 of the optic 500 can be symmetric or asymmetric and/or include higher (e.g., second, fourth, sixth, eighth) order aspheric terms. For example, the first and/or the second surface 505, 510 of the optic 500 can be described by a Zernike polynomial having upto eighth order Zernike coefficients. The first and/or second surface 505, 510 of the optic 500 can be parabolic, elliptical, a Zernike surface, an aspheric Zernike surface, a toric surface, a biconic surface, etc.

The optic 500 can be configured to provide an optical power between about 5 Diopter and +34.0 Diopter. For example, the optic 500 can be configured to provide an optical power between about 5.0 Diopter and about 10.0 Diopter, 8.0 Diopter and 15.0 Diopter, 12.0 Diopter and 20.0 Diopter, 18.0 Diopter and 25.0 Diopter, 23.0 Diopter and 30.0 Diopter, 27.0 Diopter and 34.0 Diopter or values. The optic 500 can be configured to provide cylindrical power between about 0.5 to about 5.0 Diopters to provide astigmatic correction. In various implementations, the optic 500 can be multifocal having multiple optical zones configured to provide a range of add powers between 0.5 Diopter and about 6.0 Diopter. In various implementations, the optic 500 can include filters and/or coatings to absorb short wavelengths that can damage the retina further.

Figure 6A:
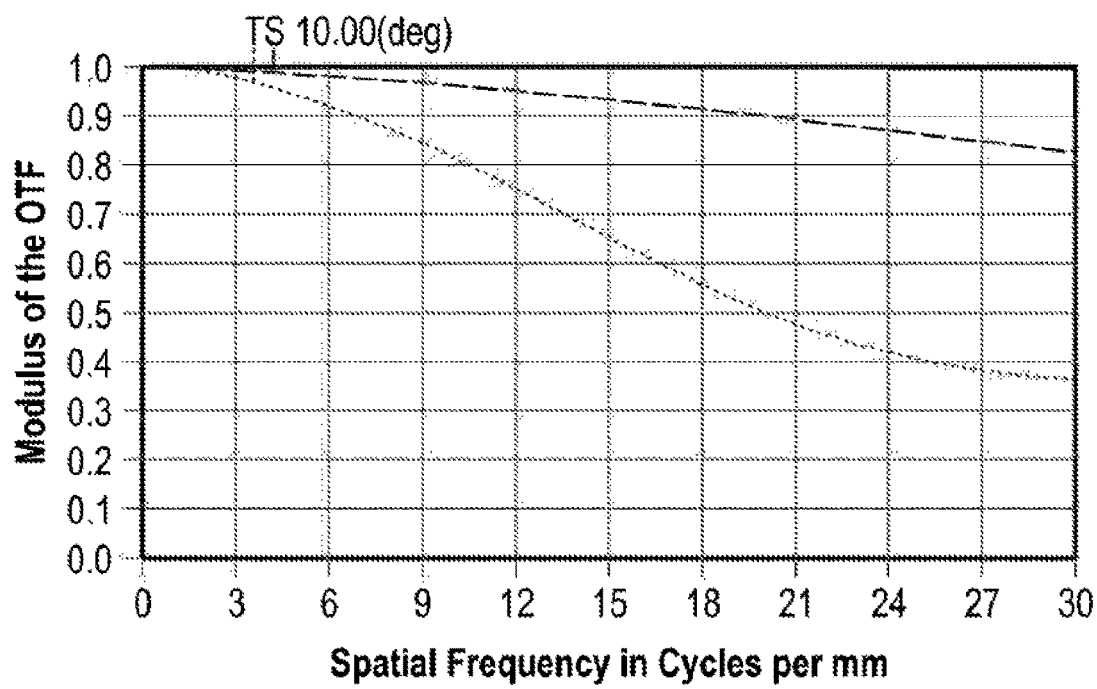
FIG. 6A shows the modulation transfer function for a standard IOL that provides good foveal vision at an eccentricity of 10 degrees.

FIG. 6A illustrates the modulus of the optical transfer function (MTF) at a PRL located at an eccentricity of 10 degrees for different spatial frequencies between 0 cycles/mm and 30 cycles/mm for a standard toric IOL (e.g., TECNIS®). As discussed above, the MTF is calculated (or simulated) for both sagittal rays and tangential rays. The MTF can be calculated (or simulated) using an optical simulation program such as, for example, OSLO, ZEMAX, CODE V, etc. As observed from FIG. 6A, the modulus of the OTF at the PRL is less than 0.4 for a spatial frequency of 30 cycles/mm for sagittal focus, while the modulus of the OTF is less than 0.9 for a spatial frequency of 30 cycles/mm for tangential focus. The patient can benefit from increase in the modulus of OTF for at least the sagittal focus.

Figure 6B:
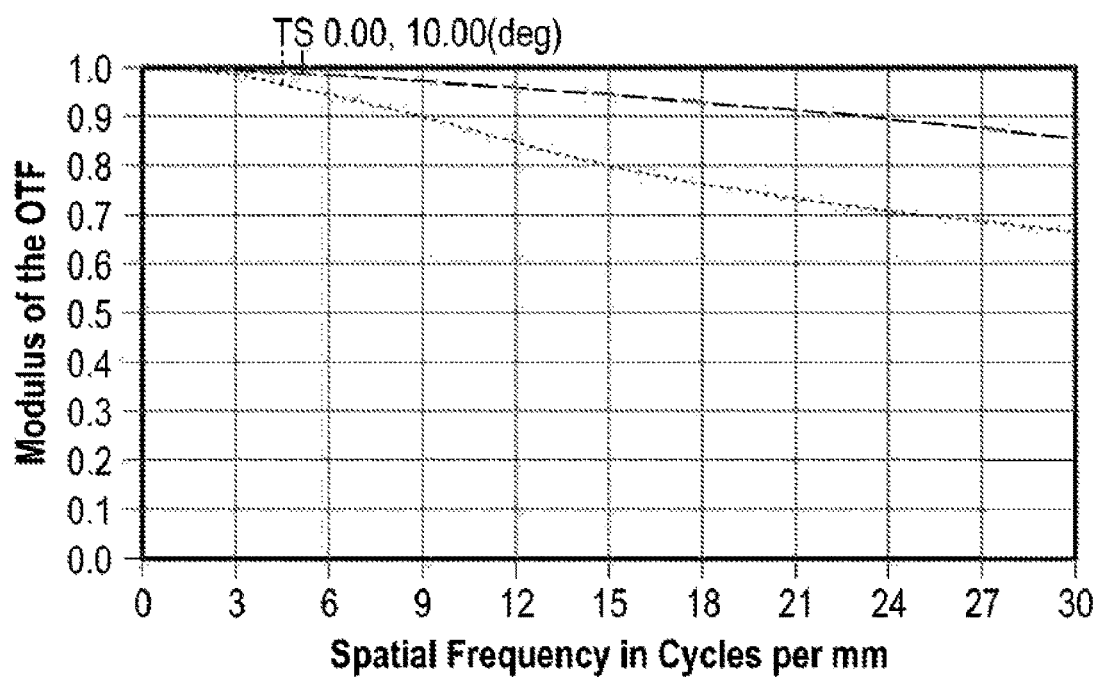
FIG. 6B shows the modulation transfer function provided by the standard toric IOL with astigmatic correction for an eccentricity of 10 degrees.
Figure 6C:
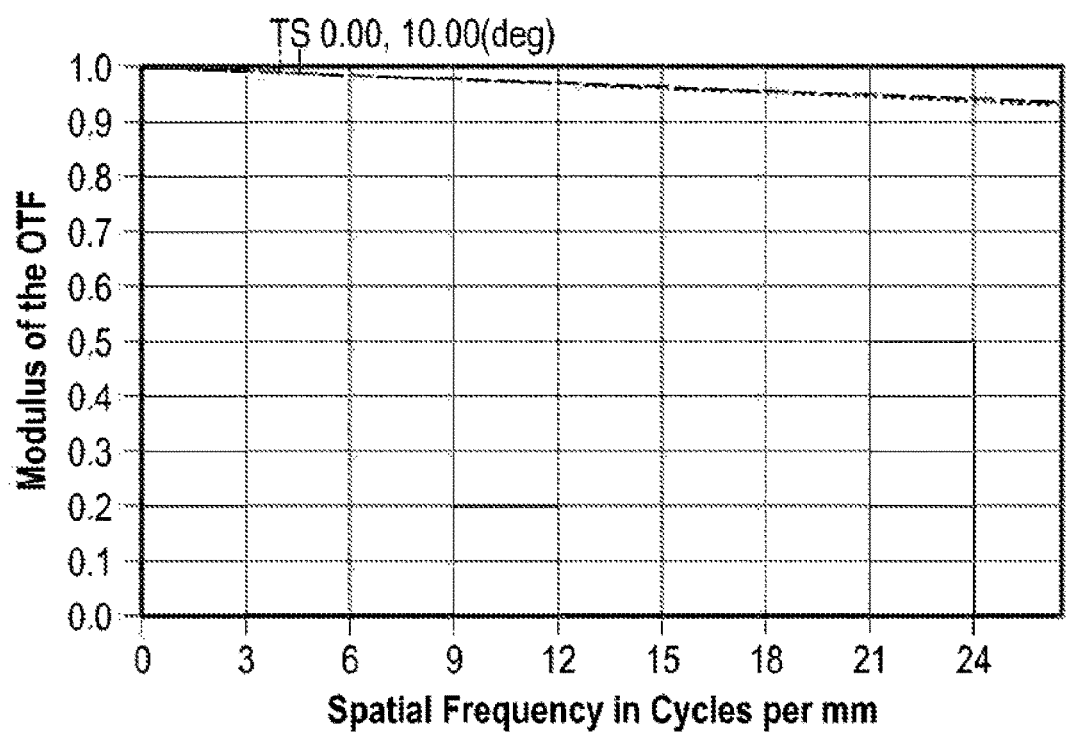
FIG. 6C shows the modulation transfer function provided by an enhanced toric IOL configured to improve visual outcome at an eccentricity of 10 degrees.

FIG. 6B illustrates the modulus of the optical transfer function (OTF) at the PRL for different spatial frequencies between 0 cycles/mm and 30 cycles/mm when the patient is implanted with a standard toric IOL that is configured to provide optimal astigmatic correction for the periphery. From FIG. 6B, it is noted that the MTF for both tangential and sagittal foci is improved as compared to a standard toric IOL and is between 0.6 and 0.7 for tangential foci for spatial frequency of 30 cycles/mm and between 0.8 and 0.9 for sagittal foci for spatial frequency of 30 cycles/mm. An optic 500 whose first surface is designed by selecting appropriate values of conic constant, astigmatic term and coma term can provide a modulus of the optical transfer function (MTF) at the PRL greater than 0.9 for both tangential and sagittal foci for spatial frequency of 30 cycles/mm as observed from FIG. 6C. Accordingly, the optic 500 described above can improve the image quality (e.g., contrast ratio of the image) at the PRL. In various implementations, the optic 500 can be configured to provide a MTF at a spatial frequency of 30 cycles/mm of at least 0.5. For example, the optic 500 can be configured to provide a MTF at a spatial frequency of 30 cycles/mm greater than 0.5, greater than 0.6, greater than 0.7, greater than 0.8 and greater than 0.9 for eccentricities between about 7 degrees and 13 degrees from the fovea.

It is conceived that the implementations of optic 500 including an enhanced toric surface that are configured to improve image quality at a peripheral retinal location by correcting optical errors arising from oblique incidence of light (e.g., oblique astigmatism and coma) can improve the MTF by at least 5% (e.g., at least 10% improvement, at least 15% improvement, at least 20% improvement, at least 30% improvement, etc.) at a spatial frequency of 30 cycles/mm for both tangential and sagittal foci at a peripheral retinal location at an eccentricity between about 1 degree and about 25 degrees with respect to the fovea as compared to the MTF at a spatial frequency of 30 cycles/mm provided by an IOL that is configured to improve image quality at the fovea at the same peripheral retinal location.

It is conceived that the implementations of optic 500 including an enhanced toric surface that are configured to improve image quality at a peripheral retinal location by correcting optical errors arising from oblique incidence of light (e.g., oblique astigmatism and coma) can provide a MTF greater than 0.2 at a spatial frequency of 30 cycles/mm for both tangential and sagittal foci, greater than 0.3 at a spatial frequency of 30 cycles/mm for both tangential and sagittal foci, greater than 0.4 at a spatial frequency of 30 cycles/mm for both tangential and sagittal foci, greater than 0.5 at a spatial frequency of 30 cycles/mm for both tangential and sagittal foci, greater than 0.6 at a spatial frequency of 30 cycles/mm for both tangential and sagittal foci, greater than 0.7 at a spatial frequency of 30 cycles/mm for both tangential and sagittal foci, greater than 0.8 at a spatial frequency of 30 cycles/mm for both tangential and sagittal foci or greater than 0.9 at a spatial frequency of 30 cycles/mm for both tangential and sagittal foci at a peripheral retinal location between about 1 degree and about 25 degrees with respect to the fovea.

Figure 7A:
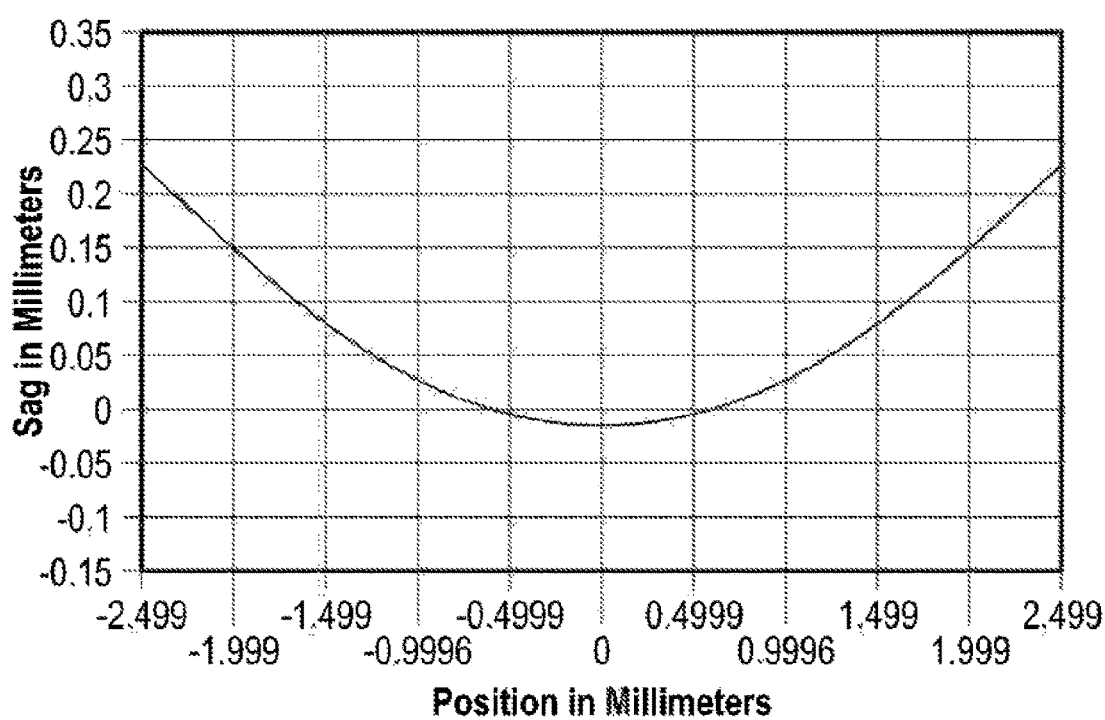
FIG. 7A illustrates the surface profile of a tilted Zernike surface in the first meridian that can provide similar visual outcome as the aspheric surface illustrated in FIG. 5A.
Figure 7B:
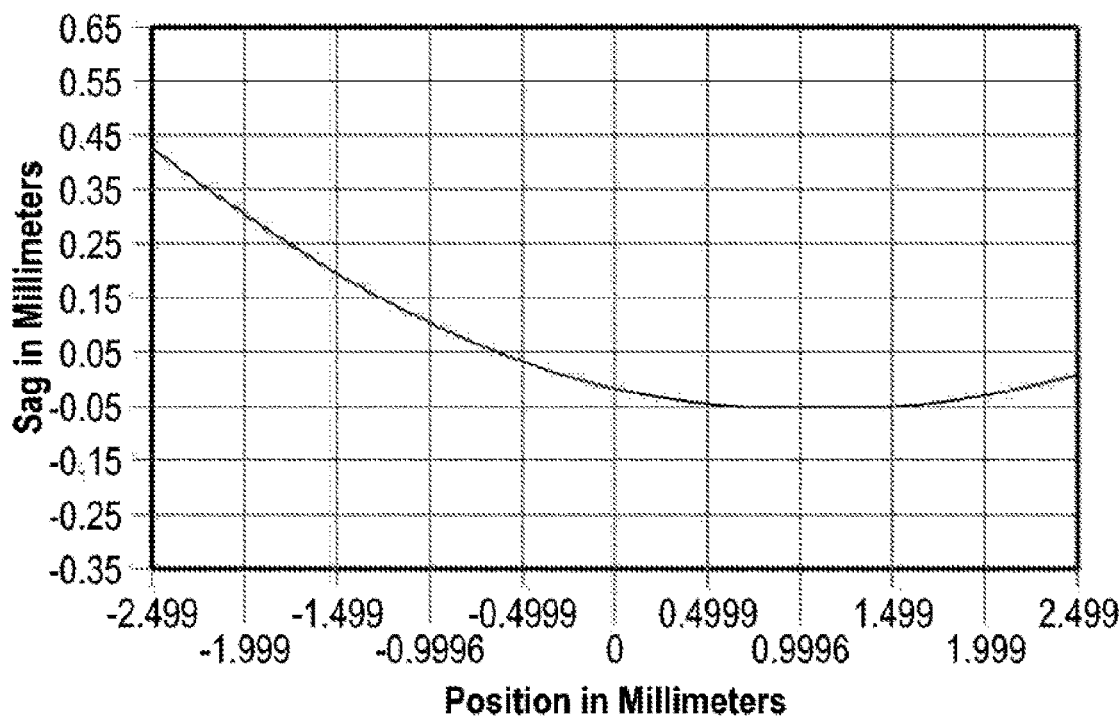
FIG. 7B illustrates the surface profile of the tilted Zernike surface in the second meridian.

A comparison of FIGS. 5B and 5C indicates that the first surface 505 of the optic 500 is not tilted with respect to the optical axis 515. It is also possible to achieve similar optical performance at a PRL located at an eccentricity of about 10 degrees as the optic 500 using an optic with a tilted Zernike surface. FIG. 7A and FIG. 7B illustrate the surface profiles along the horizontal and vertical meridians of a tilted Zernike surface that can provide similar optical performance at a PRL located at an eccentricity of about 10 degrees as the optic 500. However, the manufacturing an optic with a tilted Zernike surface can be more complicated than manufacturing an optic having a surface profile as shown in FIGS. 5B and 5C. Furthermore, when measured on-axis in air, an optic similar to optic 500 will yield measurable values for defocus, astigmatism, spherical aberration and coma. Accordingly, it is easier to evaluate the optical performance of an optic similar to optic 500 as described herein with an optical bench aberrometer as compared to other designs that have similar optical performance at the PRL. For example, a particular implementation of an optic 500 when measured in air with a 3 mm aperture using an optical bench aberrometer, had the following on-axis in focus Zernike coefficients: $A_6=2.6$ μm, $A_7=-1.07$ μm, and $A_{11}=-1.29$ μm, with all other higher order aberrations below 0.1 μm. Various implementations of the optic 500 when measured in air with a 3 mm aperture using an optical bench aberrometer can have the following values for on-axis in focus Zernike coefficients: $0 \text{ μm} \leq A_5 \leq 4$ μm, $0 \text{ μm} \leq A_6 \leq 4$ μm, $0 \text{ μm} \leq A_7 \leq 2$ μm, $0 \text{ μm} \leq A_8 \leq 2$ μm, and $0 \text{ μm} \leq A_{11} \leq 4$ μm, with all other higher order aberrations below 0.1 μm. The Zernike coefficients $A_5$ and $A_6$ are astigmatism, $A_7$ and $A_8$ are coma and $A_{11}$ is spherical aberration. Zernike coefficients $A_5$ and $A_8$ can be zero if the optic 500 is configured to provide image with reduced optical errors in the horizontal plane. However, $A_5$ and $A_8$ can be non-zero if the optic 500 is configured to provide image with reduced optical errors in the vertical plane. For example, if the PRL is at 45 degrees all coefficients will have non-zero values. However, if the PRL is vertical both $A_6$ and $A_7$ will be zero, whereas $A_5$ and $A_8$ will have non-zero values.

The optic 500 can be configured to provide one of distance vision, near vision, or intermediate distance vision, distance vision and near vision, distance vision and intermediate distance vision, near vision and intermediate distance vision or all. Various implementations of the optic 500 include spherical aberrations to correct for corneal spherical aberrations. As discussed above, diffractive optical elements can be provided on one of the surfaces (e.g., the spherical surface) of the optic 500 to provide near reading zone or to provide depth of focus. Various implementations of the optic 500 can have two astigmatic components: one determined by the angle of oblique incidence of light (or the angle the PRL makes with the optical axis of the eye) and coupled with coma correction; and one determined by corneal astigmatism and not coupled with coma correction. The optic 500 can be configured as an add-on lens that is provided in addition to an existing lens (e.g., a natural lens or another IOL) in the eye. The optic 500 can be split into two different optics: one that corrects peripheral astigmatism, and one that corrects coma. In some implementations, the optic 500 can be configured to correct errors arising only from peripheral coma or errors arising only from peripheral astigmatism. The one or more surfaces of the optic 500 can be designed for different types of patch configurations.

The optic 500 can have a clear aperture. As used herein, the term "clear aperture" means the opening of a lens or optic that restricts the extent of a bundle of light rays from a distant source that can imaged or focused by the lens or optic. The clear aperture can be circular and specified by its diameter. Thus, the clear aperture represents the full extent of the lens or optic usable for forming the conjugate image of an object or for focusing light from a distant point source to a single focus or to a plurality of predetermined foci, in the case of a multifocal optic or lens. It will be appreciated that the term clear aperture does not limit the transmittance of the lens or optic to be at or near 100%, but also includes lenses or optics having a lower transmittance at particular wavelengths or bands of wavelengths at or near the visible range of the electromagnetic radiation spectrum. In some embodiments, the clear aperture has the same or substantially the same diameter as the optic 500. Alternatively, the diameter of the clear aperture may be smaller than the diameter of the optic 500. In various implementations of the optic 500 described herein the clear aperture of the optic 500 can have a dimension between about 3.0 mm and about 7.0 mm. For example, the clear aperture of the optic 500 can be circular having a diameter of about 5.0 mm.

The optic 500 can include prismatic, diffractive elements, echellettes or optical elements with a gradient refractive index (GRIN) profile to provide a larger depth of field or near vision capability. The optic 500 can include one or more apertures in addition to the clear aperture to further enhance peripheral image quality.

The implementations of optic 500 described herein can use additional techniques to extend the depth of focus. For example, the optic 500 can include diffractive features (e.g., optical elements with a GRIN profile, echellettes, etc.) to increase depth of focus. As another example, in some embodiments, a refractive power and/or base curvature profile(s) of an intraocular lens surface(s) may contain additional aspheric terms or an additional conic constant, which may generate a deliberate amount of spherical aberration, rather than correct for spherical aberration. In this manner, light from an object that passes through the cornea and the lens may have a non-zero spherical aberration. Because spherical aberration and defocus are related aberrations, having fourth-order and second-order dependence on radial pupil coordinate, respectively, introduction of one may be used to affect the other. Such aspheric surface may be used to allow the separation between diffraction orders to be modified as compared to when only spherical refractive surfaces and/or spherical diffractive base curvatures are used. An additional number of techniques that increase the depth of focus are described in detail in U.S. patent application Ser. No. 12/971,506, titled "SINGLE MICROSTRUCTURE LENS, SYSTEMS AND METHODS," filed on Dec. 17, 2010, and incorporated by reference in its entirety herein. In some embodiments, a refractive lens may include one or more surfaces having a pattern of surface deviations that are superimposed on a base curvature (either spherical or aspheric). Examples of such lenses, which may be adapted to provide lenses according to embodiments of the present invention, are disclosed in U.S. Pat. Nos. 6,126,286, 6,923,539 and U.S. Patent Application No. 2006/0116763, all of which are herein incorporated by reference in their entirety.

Example IOL Design System

Figure 8:
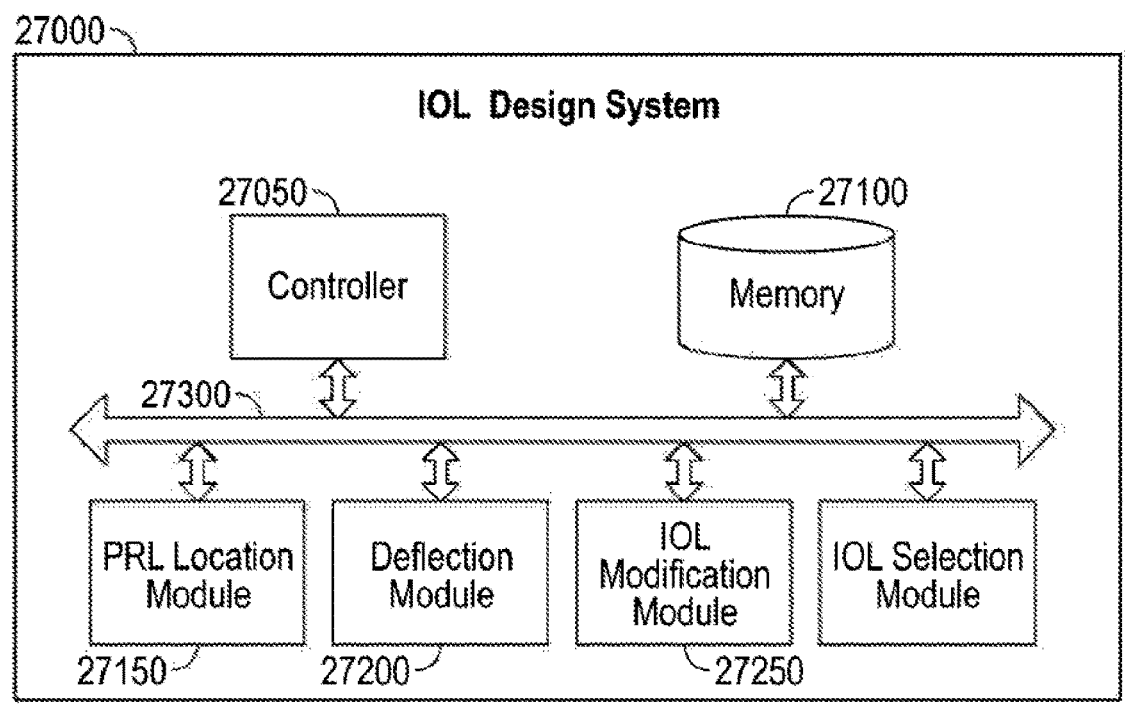
FIG. 8 illustrates a block diagram of an example IOL design system for determining properties of an intraocular lens configured to improve overall vision where there is a loss of central vision.

FIG. 8 illustrates a block diagram of an example IOL design system 27000 for determining properties of an intraocular lens configured to improve vision at a peripheral retinal location. The IOL design system 27000 includes a controller 27050 and a computer readable memory 27100 coupled to the controller 27050. The computer readable memory 27100 can include stored sequences of instructions which, when executed by the controller 27050, cause the IOL design system 27000 to perform certain functions or execute certain modules. For example, a PRL location module 27150 can be executed that is configured to determine a location of one or more PRLs for a particular patient. As another example, a deflection module 27200 can be executed that is configured to determine a deflected optical axis which intersects the determined PRL location at the retina. As another example, an IOL modification module 27250 can be executed that is configured to determine properties of the IOL which would deflect at least a portion of incident light along the determined deflected optical axis to the determined PRL. As another example, an IOL selection module 27270 can be executed that is configured to select an appropriate or candidate IOL provided one or more selection parameters including, for example and without limitation, PRL location and a patient's biometric data.

The PRL location module 27150 can be configured to determine one or more candidate PRL locations using analytical systems and methods designed to assess retinal sensitivity and/or retinal areas for fixation. For example, the PRL location module 27150 can provide or interface with a system configured to provide a patient with stimuli and to image the patient's retina to assess topographic retinal sensitivity and locations of preferred retinal loci. An example of such a system is a microperimeter which can be used to determine a patient's PRL by presenting a dynamic stimulus on a screen and imaging the retina with an infrared camera. Another example of such a system, a laser ophthalmoscope can be used to assess a retinal area used for fixation (e.g., using an infrared eye tracker) which can be used to determine discrete retinal areas for fixation for various positions of gaze.

The PRL location module 27150 can be configured to bypass the optics of the patient. In some instances, optical errors induced by a patient's optics can cause the patient to select a non-optimal PRL or a PRL which does not exhibit benefits of another PRL, e.g., where a patient selects an optically superior but neurally inferior region for the PRL. Accordingly, the PRL location module 27150 can advantageously allow the identification of a PRL which, after application of corrective optics (e.g. the IOLs described herein), would provide superior performance compared to a PRL selected utilizing a method which includes using the patient's optics. This may arise where the corrective optics reduce or eliminate the optical errors which are at least a partial cause for a patient selecting a sub-optimal PRL.

The PRL location module 27150 can be configured to determine multiple candidate locations for the PRL. The preferred or optimal PRL can be based at least upon several factors including, for example and without limitation, a patient's ability to fixate a point target, distinguish detail, and/or read; aberrations arising from redirecting images to the candidate PRL; proximity to the damaged portion of the retina; retinal sensitivity at the candidate location; and the like. The preferred or optimal PRL can depend on the visual task being performed. For example, a patient can have a first PRL for reading, a second PRL when navigating, and a third PRL when talking and doing facial recognition, etc. Accordingly, multiple PRLs may be appropriate and an IOL can be configured to redirect incident light to the appropriate PRLs using multiple zones and/or multiple redirection elements, as described herein. For example, an IOL can be provided with two or more zones, with one or more zones redirecting light to a designated PRL, where the zone can be configured to have additional optical power or no additional optical power.

The deflection module 27200 can be configured to assess the properties of the eye and to determine a deflected optical axis which intersects the patient's retina at a PRL. The deflection module 27200 can be configured to account for the removal of the natural lens, the optical properties of the cornea, the shape of the retina, the location of the PRL, axial distance from the cornea to the PRL and the like to determine the angle of deflection from the eye's natural optical axis (e.g., the optical axis of the natural lens, the optical axis of the eye without an IOL, etc.). In some embodiments, the deflection module 27200 can be configured to determine aberrations arising from deflecting incident light along the deflected optical axis. The aberrations can include astigmatism, coma, field curvature, etc. The determined aberrations can be used in the process of refining or tailoring the design of the IOL, where the IOL is configured to at least partially correct or reduce the determined aberrations.

The IOL modification module 27250 can be configured to determine adjustments, modifications, or additions to the IOL to deflect light along the deflected optical axis and focus images on the PRL. Examples of adjustments, modifications, or additions to the IOL include, without limitation, the optical systems and methods described herein. For example, the IOL can be modified through the introduction of a physical and/or optical discontinuity to deflect and focus light onto the PRL. As another example, one or more redirection elements can be added to one or more surfaces of the IOL to redirect at least a portion of the light incident on the eye to the PRL. The redirection elements can include, for example and without limitation, a simple prism, a Fresnel prism, a redirection element with a tailored slope profile, redirection element with a tailored slope profile tuned to reduce optical aberrations, a diffraction grating, a diffraction grating with an achromatic coating, a decentered GRIN lens, etc. In some embodiments, multiple redirection elements and/or multiple modifications can be made to the IOL, as determined by the IOL modification module 27250, such that the combination of modifications and/or additions to the IOL can be configured to redirect incident light to different PRLs, to direct incident light to different portions of the retina, to provide an optical power which magnifies an image at the retina, or any combination of these functions.

The IOL selection module 27270 can be configured to select the IOL design, power, deflection, orientation, and the like that would provide acceptable or optimal results for a particular patient. The IOL selection can be based at least in part on the patient's biometric inputs. The IOL selection can incorporate multiple considerations. For example, typical IOL power calculation procedures can be used to select the spherical IOL power which can be modified to consider the axial distance from the cornea to the PRL. As another example, customized or additional constants can be developed for AMD patients which provide better results for the patients. The deflection and orientation of the IOL during implantation would be given by the PRL location.

The IOL selection can be based at least in part on ray tracing which can enable a computational eye model of the patient to be generated where the inputs can be the patient's own biometric data. The optical quality can be evaluated considering different IOL deigns and powers, being selected that which optimizes the optical quality of the patient. The optical quality can be evaluated at the PRL or at the PRL and on-axis, for example.

In some embodiments, the IOL selection module 27270 can also comprise a refractive planner which shows patients the expected outcome with different IOL designs and options. This can enable the patient to aid in the decision as to the appropriate IOL design and to come to a quick and satisfactory solution.

The IOL design system 27000 can include a communication bus 27300 configured to allow the various components and modules of the IOL design system 27000 to communicate with one another and exchange information. In some embodiments, the communication bus 27300 can include wired and wireless communication within a computing system or across computing systems, as in a distributed computing environment. In some embodiments, the communication bus 27300 can at least partially use the Internet to communicate with the various modules, such as where a module (e.g., any one of modules 27150, 27200, or 27250) incorporated into an external computing device and the IOL design system 27000 are communicably coupled to one another through the communication bus 27300 which includes a local area network or the Internet.

The IOL design system 27000 may be a tablet, a general purpose desktop or laptop computer or may comprise hardware specifically configured for performing the programmed calculations. In some embodiments, the IOL design system 27000 is configured to be electronically coupled to another device such as a phacoemulsification console or one or more instruments for obtaining measurements of an eye or a plurality of eyes. In certain embodiments, the IOL design system 27000 is a handheld device that may be adapted to be electronically coupled to one of the devices just listed. In some embodiments, the IOL design system 27000 is, or is part of, a refractive planner configured to provide one or more suitable intraocular lenses for implantation based on physical, structural, and/or geometric characteristics of an eye, and based on other characteristics of a patient or patient history, such as the age of a patient, medical history, history of ocular procedures, life preferences, and the like.

Generally, the instructions stored on the IOL design system 27000 will include elements of the methods 2900, and/or parameters and routines for solving the analytical equations discussed herein as well as iteratively refining optical properties of redirection elements.

In certain embodiments, the IOL design system 27000 includes or is a part of a phacoemulsification system, laser treatment system, optical diagnostic instrument (e.g, autorefractor, aberrometer, and/or corneal topographer, or the like). For example, the computer readable memory 27100 may additionally contain instructions for controlling the handpiece of a phacoemulsification system or similar surgical system. Additionally or alternatively, the computer readable memory 27100 may contain instructions for controlling or exchanging data with one or more of an autorefractor, aberrometer, tomographer, microperimeter, laser ophthalmoscope, topographer, or the like.

In some embodiments, the IOL design system 27000 includes or is part of a refractive planner. The refractive planner may be a system for determining one or more treatment options for a subject based on such parameters as patient age, family history, vision preferences (e.g., near, intermediate, distant vision), activity type/level, past surgical procedures.

Additionally, the solution can be combined with a diagnostics system that identifies the best potential PRL after correction of optical errors. Normally, optical errors can restrict the patient from employing the best PRL, making them prefer neurally worse but optically better region. Since this solution would correct the optical errors, it is important to find the best PRL of the patient with a method that is not degraded by optical errors (e.g. adaptive optics). Finally, the solution can be utilized to take advantage of the symmetries that exists with regards to peripheral optical errors in many patients.

Prior to replacing a natural crystalline lens with an IOL, an optical power of the IOL is typically determined. Generally, the on-axis axial length, corneal power of the eye, and/or additional parameters can be used to determine the optical power of the IOL to achieve a targeted refraction with a goal of providing good or optimal optical quality for central/foveal vision. However, where there is a loss of central vision an IOL configured to provide good or optimal optical quality for central vision may result in relatively high peripheral refraction and reduced or unacceptable optical quality at a peripheral location on the retina. Accordingly, systems and methods provided herein can be used to tailor the optical power of an IOL to provide good or optimal optical quality at a targeted peripheral location such as a patient's PRL. The improvement in optical quality at the peripheral retinal location may reduce the optical quality at the fovea, but this may be acceptable where the patient is suffering from a loss in central vision.

Figure 9:
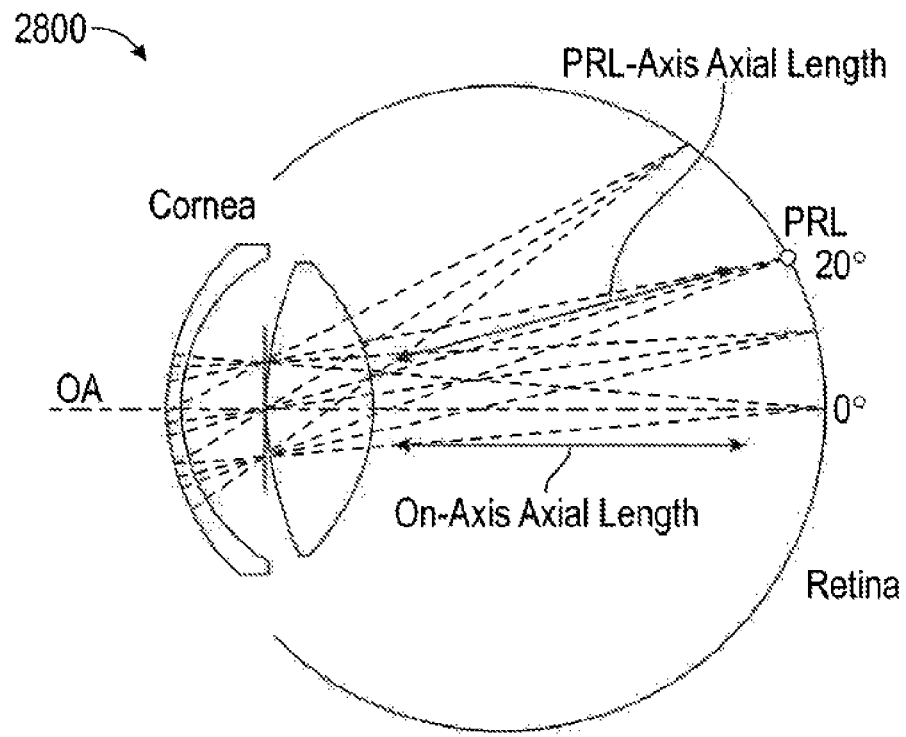
FIG. 9 illustrates parameters used to determine an optical power of an IOL based at least in part on a location of a PRL in a patient.

FIG. 9 illustrates parameters used to determine an optical power of an IOL based at least in part at a peripheral retinal location in an eye 2800. The eye 2800 is illustrated with a PRL location at 20 degrees with respect to the optical axis OA. This can represent an intended post-operative PRL location, where the PRL location is determined as described elsewhere herein. The on-axis axial length (e.g., axial length along optical axis OA) and PRL-axis axial length (e.g., axial length along a deflected optical axis intersecting the retina at the PRL) can be measured for the eye 2800 having the indicated PRL location. In some patients, the axial length in the direction of the PRL can be estimated from the measured on-axis axial length and population averages of ocular characteristics measured using a diagnostic instrument. The ocular characteristics measured using the diagnostic instrument can include pre-operative refraction, corneal power or other parameters. The corneal topography can also be measured (e.g., measurements of the anterior and posterior surfaces of the cornea, thickness of the cornea, etc.) and these measurements can be used, at least in part, to determine the corneal power.

Figure 10A:
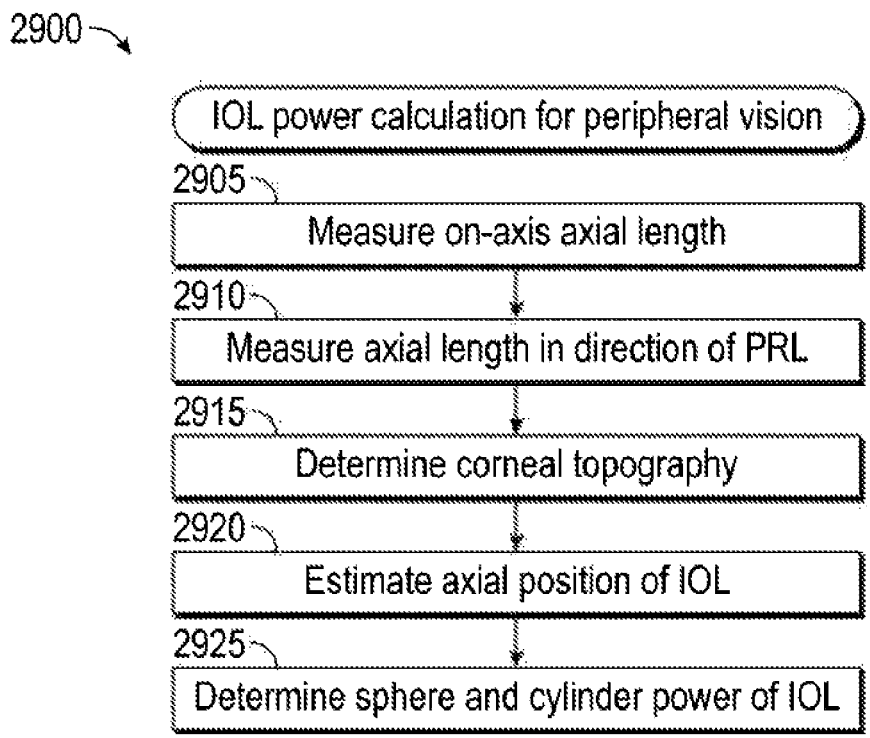
FIG. 10A and FIG. 10B illustrate implementations of a method for determining an optical power of an IOL tailored to improve peripheral vision.
Figure 10B:
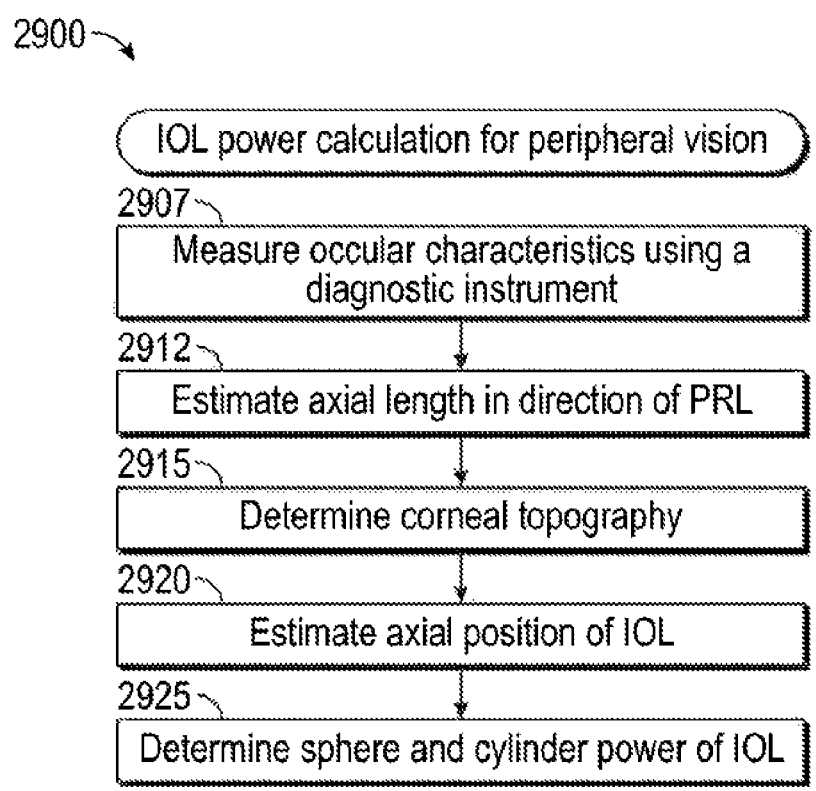

FIGS. 10A and 10B illustrate implementations of a method 2900 for determining an optical power of an IOL tailored to improve peripheral vision. For reference, FIG. 9 provides an illustration of an eye 2800 for which the method 2900 can be applied. In addition, FIG. 8 provides a block diagram of the IOL design system 27000 which can perform one or more operations of the method 2900. The method 2900 can be used to determine the optical power of the IOL which improves or optimizes optical quality at a PRL location. However, the method 2900 can be used to determine the optical power of an IOL to be used in any suitable procedure, such as where there is a loss of central vision, where the PRL is outside the fovea, where the PRL is within the fovea, where there are multiple PRLs, where the PRL is at a relatively large or small eccentricity, or the like.

With reference to FIGS. 10A and 10B, in block 2905, the on-axis axial length is measured. The on-axis axial length can be measured, for example, from the anterior surface of the cornea to the retina. The length can be determined using any number of standard techniques for making measurements of the eye. In some embodiments, instead of measuring the on-axis axial length, it is estimated based on computer models of eyes, statistical data (e.g., average on-axis distance for eyes with similar characteristics), or a combination of these. In some embodiments, the on-axis axial length is determined using a combination of measurement techniques and estimation techniques.

With reference to FIG. 10A, in block 2910, the PRL-axis axial length is measured. The PRL-axis axial length can be taken as the length along a deflected optical axis to the PRL location at the retina. The length can be measured from the anterior surface of the cornea, from the point of deflection from the optical axis, or any other suitable location. In some embodiments, the PRL-axis axial length can be estimated based on a combination of the eccentricity of the PRL, the PRL location, the retinal shape, the on-axis axial length, the distance from a proposed IOL location to the PRL, or any combination of these. In some embodiments, instead of measuring the PRL-axis axial length, it is estimated based on computer models of eyes, statistical data (e.g., average PRL-axis axial length for eyes with similar PRL locations and characteristics), or a combination of these. In some embodiments, the PRL-axis axial length is determined using a combination of measurement techniques and estimation techniques. In some embodiments, the PRL-axis axial length can be estimated based on population averages of ocular characteristics measured using a diagnostic instrument, as shown in block 2907 and 2912 of FIG. 10B. The measured ocular characteristics can include on-axis axial length, pre-operative refraction power, corneal power or other measured parameters.

In block 2915, the corneal shape is determined. The anterior and/or posterior surfaces of the cornea can be determined using measurements, estimations, simulations, or any combination of these. The corneal power can be derived or determined based at least in part on the corneal shape, that can be measured with tomography or topographic techniques. In some embodiments, the corneal power is determined based on measurements of optical properties of the cornea.

In block 2920, the position of the IOL is estimated. The position of the IOL can be estimated based at least in part on an estimation of a location which would provide good optical quality at the fovea. The location can be one that takes into account the corneal power or topography and the on-axis axial length. Some other inputs that can be taken into consideration to predict the postoperative IOL position are the axial position of the crystalline lens from the anterior cornea, which is defined as anterior chamber depth, crystalline lens thickness, vitreous length on axis combinations of thereof. In some embodiments, the estimated position of the IOL can be refined by taking into account the PRL-axis axial length and/or eccentricity of the PRL. In some embodiments, the estimated IOL location can take into account data from previous procedures, with or without including the same IOL design. For example, historic data from cataract surgeries can be used as that data may indicate a good estimate of the IOL position.

In some embodiments, rather than determining an estimated initial position of the IOL configured to provide good optical quality for central/foveal vision, the estimated position can be configured to provide good optical quality for peripheral vision. Similar procedures as described for determining the IOL position that provides with good optical quality on axis can be applied in this case. Therefore, the location of the IOL can be predicted from biometric measurements, including corneal shape or power, axial length, either on axis or to the PRL, anterior chamber depth, crystalline lens thickens and/or vitreous length, either defined on axis or to the PRL. Retrospective data from previous cataract procedures aimed to restore vision on axis or at the PRL can also been taken into consideration to optimize the prediction of the IOL position that provide with good optical quality at the PRL. In addition to that, the estimated position can be based at least in part on procedures, for example, where the patient was suffering from central vision loss (e.g., due to AMD). Similarly, data can be used where the positions of IOLs have been tabulated and recorded as a function of the properties of the IOLs (e.g., sphere power, cylinder power, cylinder axis, redirection angle, etc.) and such properties were tailored using the systems and methods described herein. Data from such procedures can be subjected to further selection criteria based on the location of the PRLs of the patients, where the locations were, for example and without limitation, outside a determined angular range of the fovea, at an eccentric angle greater and/or less than a threshold eccentricity, at an eccentricity within a provided range of the PRL of the patient, or any combination of these. The data can be selected based on these criteria or other similar criteria which may improve the estimated IOL position for patients suffering from a loss of central vision.

In block 2925, the sphere and cylinder power of the IOL is determined using an IOL power calculation. The IOL power calculation can be configured to provide a spherical power for the IOL, a cylinder power for the IOL, and/or the cylinder axis, wherein the combination of one or more of these parameters is configured to provide good or optimal optical quality at the PRL location when the IOL is implanted at the estimated location.

The IOL power calculation can use as input data, for example and without limitation, on-axis axial length (e.g., the measurement or value provided in block 2905), corneal power (e.g., the value determined from measurements acquired in block 2915), fixation angle(s) (e.g., horizontal and vertical angles of fixation), intended post-operative refraction, eccentricity of the PRL, eccentric axial length (e.g., from the anterior cornea to the location of the PRL on the retina, such as the measurement or value provided in block 2910), predicted future movement of the PRL (e.g., due to progression of a disease such as AN/ID), a partial or full map of the retinal shape, a partial or full map of the retinal health, corneal topography, or the like. In some embodiments, the IOL power calculation is a regression formula, a theoretical formula (e.g., based on paraxial optical equations, ray tracing, etc.), or a combination of both of these. In some embodiments, current IOL power calculation procedures can be used while considering the eccentric axial length together with the corneal power. In those cases, A constants for either lenses to restore vision on axis after cataract surgery can be used. In certain embodiments, specific A constants can be determined depending on the design and/or eccentricity.

In some embodiments, ray tracing can be used to determine properties of the IOL which improve or reduce peripheral errors at the PRL based at least in part on the estimated IOL position. The ray tracing can incorporate relevant measurements and data including, for example and without limitation, the measurements of the eye (e.g., the measurements or values determined in blocks 2905, 2910, and 2915), the position of the PRL, the estimated position of the IOL (e.g., as provided in block 2920), and the like. This information can be used as input in a computer executable module or program stored in non-transitory computer memory, the module or program configured to cause a computer processor to execute instructions configured to perform ray tracing which can be accomplished, for example, by the IOL design system 27000 described herein with reference to FIG. 8. The ray tracing system can be used to find the sphere power, cylinder power, and/or cylinder axis of the IOL to be implanted in the eye 2800, wherein these parameters are tailored to improve or optimize for peripheral aberrations at the PRL location. Any standard ray tracing system or scheme can be used to accomplish the goal of tailoring the sphere power, cylinder power, and/or cylinder axis.

In some embodiments, the output of the IOL power calculation can be used for selecting an appropriate or suitable IOL where the output of the IOL power calculation includes, for example and without limitation, dioptric power, cylinder power, cylinder axis, deflection angle, and the like. These output values can be used in the selection of the IOL wherein the selected IOL has one or more properties within an acceptable range of the output values. In some embodiments, the IOL power calculation can be used to define or select IOL design parameters that improve or optimize optical quality as a function of retinal location(s) or retinal area(s).

In some embodiments, the IOL power calculation can be similar or equivalent to a power calculation configured to provide good or optimal on-axis optical quality (e.g., for central/foveal vision) where the axial length used is the PRL-axis axial length rather than the on-axis axial length. In some embodiments, the PRL-axis axial length can be determined based at least in part on the eccentricity of the PRL, the PRL location, the retinal shape, the length from the IOL to the PRL, or any combination of these. These and other input values can be determined based on measurements of a particular patient (e.g., the patient to receive the IOL), a group of patients, from computer models or simulations, or a combination of these sources. In an alternative embodiment, both, the axial length on axis and to the PRL can be considered, so that the IOL selected is that which maximizes the optical quality at the PRL and at, to some extended, at the fovea. In another embodiment, the axial length to several PRL can be considered, so that the IOL selected is that which has the characteristics that optimize the optical quality at each PRL.

In some embodiments, the IOL power calculation can be used for multifocal IOLs for patients suffering from a loss of central vision. The IOL power calculation can be configured to provide valid and acceptable results where the PRL lies within the fovea. In an alternative embodiment the add power of the multifocal IOL can be selected as that which maximizes the optical quality either at the PRL and/or the fovea.

In some embodiments, the IOL power calculation can be used in conjunction with the other systems and methods described herein configured to redirect and focus images to the PRL. The power calculations can be used to tailor the properties of the IOL, the IOL being used in combination with one or more redirection elements to reduce peripheral aberrations and/or improve peripheral image quality for patients suffering from a loss of central vision.

Additional Embodiments for Selecting IOL Sphere and Cylinder

As detailed above, IOL power is typically selected based primarily on axial length and corneal power, and any toric parts mostly depend on the toricity of the cornea. However, any spherical surface for which the light is obliquely incident will exhibit a large degree of astigmatism. The embodiments below detail additional ways to properly select sphere and cylinder of the IOL for the AMD patient.

In one embodiment, sphere selection is based on population data. Here, no new biometry readings are needed. Instead, the patients are classified depending on foveal refraction, from which the average peripheral spherical profile for that refractive group is selected. From the profile, spherical refraction at the PRL can be determined.

As seen above, sphere selection may also be based on individual data. The peripheral sphere can be determined through an axial length measurement to the PRL. This requires the modification of current axial length methods, since the oblique incidence on the crystalline lens will mean a longer than average passage through the lens, which has a higher index of refraction, increasing the difference between the optical path length and the physical length. The increased contribution can be predicted based on PRL location.

In one embodiment, astigmatism determination is based on population data. The inter-subject variation in astigmatism for a given angle is relatively modest. Therefore, the contribution of the oblique incidence at any given eccentricity can be predicted based on PRL location. For these calculations, PRL location should be determined based on the optical axis, which is on average between about 1-10 degrees horizontally and between about 1-5 degrees vertically from the fovea. The axis of the astigmatism can also be determined from the location, e.g. for a horizontal PRL the axis is 180 and for a vertical PRL the axis is 90, for a negative cylinder convention. Additionally, the astigmatism contribution of the IOL selected can be incorporated, in an iterative selection procedure. To this astigmatism, the corneal astigmatism from the cornea can also be added.

In another embodiment, astigmatism determination is based on individual data. Even for persons that are foveally emmetropic, the oblique astigmatism at e.g. 20 degrees can vary between 0.75 D and 2 D. There are several possible reasons for this: 1) The individual differences in angle between fovea and optical axis; 2) Individual differences in corneal power means the oblique astigmatism has different values; 3) Pupil position relative lens and cornea can be different leading to variation in the IOL position for different individuals. Biometry reading for any or all of these parameters can then be incorporated into an individual eye model, to select the best IOL cylinder power for the patient.

CONCLUSION

The above presents a description of systems and methods contemplated for carrying out the concepts disclosed herein, and of the manner and process of making and using it, in such full, clear, concise, and exact terms as to enable any person skilled in the art to which it pertains to make and use this invention. The systems and methods disclosed herein, however, are susceptible to modifications and alternate constructions from that discussed above which are within the scope of the present disclosure. Consequently, it is not the intention to limit this disclosure to the particular embodiments disclosed. On the contrary, the intention is to cover modifications and alternate constructions coming within the spirit and scope of the disclosure as generally expressed by the following claims, which particularly point out and distinctly claim the subject matter of embodiments disclosed herein.

Although embodiments have been described and pictured in an exemplary form with a certain degree of particularity, it should be understood that the present disclosure has been made by way of example, and that numerous changes in the details of construction and combination and arrangement of parts and steps may be made without departing from the spirit and scope of the disclosure as set forth in the claims hereinafter.

As used herein, the term "controller" or "processor" refers broadly to any suitable device, logical block, module, circuit, or combination of elements for executing instructions. For example, the controller 27050 can include any conventional general purpose single- or multi-chip microprocessor such as a Pentium® processor, a MIPS® processor, a Power PC® processor, AMD® processor, ARM processor, or an ALPHA® processor. In addition, the controller 27050 can include any conventional special purpose microprocessor such as a digital signal processor. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Controller 27050 can be implemented as a combination of computing devices, e.g., a combination of a DSP and a microprocessor, a plurality of microprocessors, one or more microprocessors in conjunction with a DSP core, or any other such configuration.

Computer readable memory 27100 can refer to electronic circuitry that allows information, typically computer or digital data, to be stored and retrieved. Computer readable memory 27100 can refer to external devices or systems, for example, disk drives or solid state drives. Computer readable memory 27100 can also refer to fast semiconductor storage (chips), for example, Random Access Memory (RAM) or various forms of Read Only Memory (ROM), which are directly connected to the communication bus or the controller 27050. Other types of memory include bubble memory and core memory. Computer readable memory 27100 can be physical hardware configured to store information in a non-transitory medium.

Methods and processes described herein may be embodied in, and partially or fully automated via, software code modules executed by one or more general and/or special purpose computers. The word "module" can refer to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

What is claimed is:

1. An optic configured to improve vision for a patient's eye, the optic comprising:
   a surface configured to improve image quality of an image produced by light incident on the patient's eye at an oblique angle with respect to an optical axis intersecting the eye and focused at a peripheral retinal location disposed at a distance from the fovea,
   wherein the image quality is improved by reducing oblique astigmatism at the peripheral retinal location,
   wherein a modulation transfer function (MTF) of the optic at one or more spatial frequencies for light incident on the optic and forming an image at the peripheral retinal location at an eccentricity having a value between about 1 degree and about 25 degrees is greater than a modulation transfer function (MTF) of the optic at one or more spatial frequencies for light incident on the optic and forming an image at the peripheral retinal location at an eccentricity having a value between 0 degrees and less than 1 degree.

2. The optic of claim 1, wherein the image quality is improved by reducing coma at the peripheral retinal location.

3. The optic of claim 1 configured to provide astigmatic correction of at least 0.5 Diopter at the peripheral retinal location.

4. The optic of claim 1 configured to provide at least 0.1 μm of coma correction at the peripheral retinal location for a 6 mm pupil.

5. The optic of claim 1, wherein the oblique angle is between about 1 degree and about 25 degrees.

6. The optic of claim 1, wherein the surface is a Zernike surface having a radius of curvature between about 5 mm and about 25 mm.

7. The optic of claim 6, wherein the Zernike surface has a conic constant between about 0 and about −100.

8. The optic of claim 6, wherein the Zernike surface has an astigmatic coefficient between about 0 μm and about 4 μm.

9. The optic of claim 6, wherein the Zernike surface has a coma coefficient between about 0 μm and about 2 μm.

10. The optic of claim 1, wherein the surface has a spherical aberration coefficient with a value between 0 μm and 4 μm when measured in air with a 3 mm aperture using an optical bench aberrometer.

11. The optic of claim 1, further comprising a spherical surface opposite the surface.

12. The optic of claim 11, wherein the spherical surface comprises one or more diffractive elements.

13. The optic of claim 1, configured to be implanted in the eye of a patient.

14. The optic of claim 1, further comprising prismatic features.

15. The optic of claim 1, wherein the optic has a modulation transfer function (MTF) of at least 0.3 for a spatial frequency of 30 cycles/mm for both the tangential and the sagittal foci at the peripheral retinal location.

* * * * *